US011155267B2

(12) United States Patent
Absmeier et al.

(10) Patent No.: US 11,155,267 B2
(45) Date of Patent: Oct. 26, 2021

(54) MOBILE SENSOR PLATFORM

(71) Applicant: Samsung Electronics Co., Ltd., Suwon-si (KR)

(72) Inventors: John Absmeier, Capitola, CA (US); David Anderson, Royal Oak, MI (US); Rafel Fors Perez, San Jose, CA (US); Yosi Levi, Menlo Park, CA (US); Anthony Nguyen, Fremont, CA (US); Eunsung Park, San Jose, CA (US); Divya Shah, Sunnyvale, CA (US); Euan Thomson, Los Gatos, CA (US)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 44 days.

(21) Appl. No.: 15/697,382

(22) Filed: Sep. 6, 2017

(65) Prior Publication Data
US 2018/0099678 A1 Apr. 12, 2018

Related U.S. Application Data

(60) Provisional application No. 62/406,912, filed on Oct. 11, 2016.

(51) Int. Cl.
G01C 22/00 (2006.01)
B60W 40/08 (2012.01)
(Continued)

(52) U.S. Cl.
CPC .......... B60W 40/08 (2013.01); A61B 5/0077 (2013.01); A61B 5/02055 (2013.01); A61B 5/165 (2013.01); A61B 5/18 (2013.01); A61B 5/318 (2021.01); A61B 5/369 (2021.01); A61B 5/4803 (2013.01); A61B 5/6893 (2013.01); A61B 5/747 (2013.01); A61B 7/003 (2013.01); A61M 21/0094 (2013.01); A61M 21/02 (2013.01); B60R 16/037 (2013.01); G05D 1/0088 (2013.01); G16H 40/67 (2018.01); A61B 5/021 (2013.01); A61B 5/053 (2013.01); A61B 5/082 (2013.01); A61B 5/14542 (2013.01); A61M 2021/0016 (2013.01);
(Continued)

(58) Field of Classification Search
CPC ....... B60W 40/08; G16H 40/67; A61B 5/369; A61B 5/318; A61B 5/0077; A61B 5/02055; A61B 5/165; A61B 5/18; A61B 5/4803; A61B 5/6893; A61B 5/747; A61B 7/003; A61M 21/0094; A61M 21/02
See application file for complete search history.

(56) References Cited

U.S. PATENT DOCUMENTS 8,738,197 B2   5/2014   An et al.
9,826,499 B2   11/2017  Han et al.
(Continued)

FOREIGN PATENT DOCUMENTS

CN   105059214   11/2015
CN   105138044   12/2015
(Continued)

Primary Examiner — Adam M Alharbi
(74) Attorney, Agent, or Firm — F. Chau & Associates, LLC

(57) ABSTRACT

Provided is a disclosure for a mobile sensor platform including various hardware and software to perform sensing operations of various occupants in the mobile sensor platform.

18 Claims, 11 Drawing Sheets

(51) Int. Cl.

| | | |
|---|---|---|
| *A61M 21/00* | (2006.01) | |
| *G16H 40/67* | (2018.01) | |
| *A61B 5/318* | (2021.01) | |
| *A61B 5/369* | (2021.01) | |
| *A61B 5/00* | (2006.01) | |
| *A61B 5/0205* | (2006.01) | |
| *A61B 5/16* | (2006.01) | |
| *A61B 5/18* | (2006.01) | |
| *A61B 7/00* | (2006.01) | |
| *A61M 21/02* | (2006.01) | |
| *B60R 16/037* | (2006.01) | |
| *G05D 1/00* | (2006.01) | |
| *A61B 5/021* | (2006.01) | |
| *A61B 5/053* | (2021.01) | |
| *A61B 5/08* | (2006.01) | |
| *A61B 5/145* | (2006.01) | |
| *G06Q 30/06* | (2012.01) | |
| *G06Q 50/12* | (2012.01) | |

(52) U.S. Cl.
CPC .............. *A61M 2021/0027* (2013.01); *A61M 2021/0044* (2013.01); *A61M 2021/0066* (2013.01); *A61M 2205/332* (2013.01); *A61M 2205/3303* (2013.01); *A61M 2230/06* (2013.01); *A61M 2230/205* (2013.01); *A61M 2230/30* (2013.01); *A61M 2230/42* (2013.01); *A61M 2230/50* (2013.01); *A61M 2230/63* (2013.01); *B60W 2040/0818* (2013.01); *B60W 2040/0872* (2013.01); *B60W 2540/22* (2013.01); *G06Q 30/0631* (2013.01); *G06Q 50/12* (2013.01)

(56) References Cited

U.S. PATENT DOCUMENTS

| | | | |
|---|---|---|---|
| 10,241,509 B1* | 3/2019 | Fields | ................ G06Q 30/0207 |
| 2007/0193798 A1 | 8/2007 | Allard et al. | |
| 2010/0240299 A1 | 9/2010 | Karino | |
| 2017/0075355 A1 | 3/2017 | Micks et al. | |
| 2017/0282717 A1* | 10/2017 | Jang | ........................ B60K 37/06 |
| 2018/0093631 A1* | 4/2018 | Lee | ........................ B60W 50/082 |
| 2018/0178781 A1* | 6/2018 | Funk | ........................ H04W 4/70 |
| 2018/0181094 A1* | 6/2018 | Funk | ........................ H04W 4/70 |
| 2018/0181095 A1* | 6/2018 | Funk | ........................ G05B 19/042 |
| 2018/0229721 A1 | 8/2018 | Li | |

FOREIGN PATENT DOCUMENTS

| | | |
|---|---|---|
| DE | 102011085976 | 5/2013 |
| JP | 2001-195692 | 7/2001 |
| JP | 2010-220050 | 9/2010 |
| JP | 2011065400 | 3/2011 |
| JP | 2011-221898 | 11/2011 |
| KR | 10-2011-0058384 | 6/2011 |
| KR | 10-2014-0074782 | 6/2014 |

\* cited by examiner

MOBILE SENSOR PLATFORM

RELATED APPLICATION

This application claims the benefit of priority to the U.S. Provisional Application 62/406,912, filed on Oct. 11, 2016, the disclosure of which is incorporated herein in its entirety by reference.

BACKGROUND

The present invention relates to vehicles, and more particularly, to a mobile vehicle platform. Various efforts are under way for controlling various aspects of a vehicle.

Various limitations and disadvantages of conventional and traditional approaches will become apparent to one of skill in the art, through comparison of such systems with some aspects of the present disclosure as set forth in the remainder of this application with reference to the drawings.

SUMMARY

A system and/or method for an apparatus and method for a mobile vehicle platform, substantially as shown in and/or described in connection with at least one of the drawings.

Various advantages, aspects, and novel features of the present invention, as well as details of an illustrated embodiment thereof, will be more fully understood from the following description and drawings.

BRIEF DESCRIPTION OF THE DRAWINGS

The above and other objects, features and advantages of the present disclosure will become more apparent from the following detailed description when taken in conjunction with the accompanying drawings in which.

DETAILED DESCRIPTION

Figure 1A:
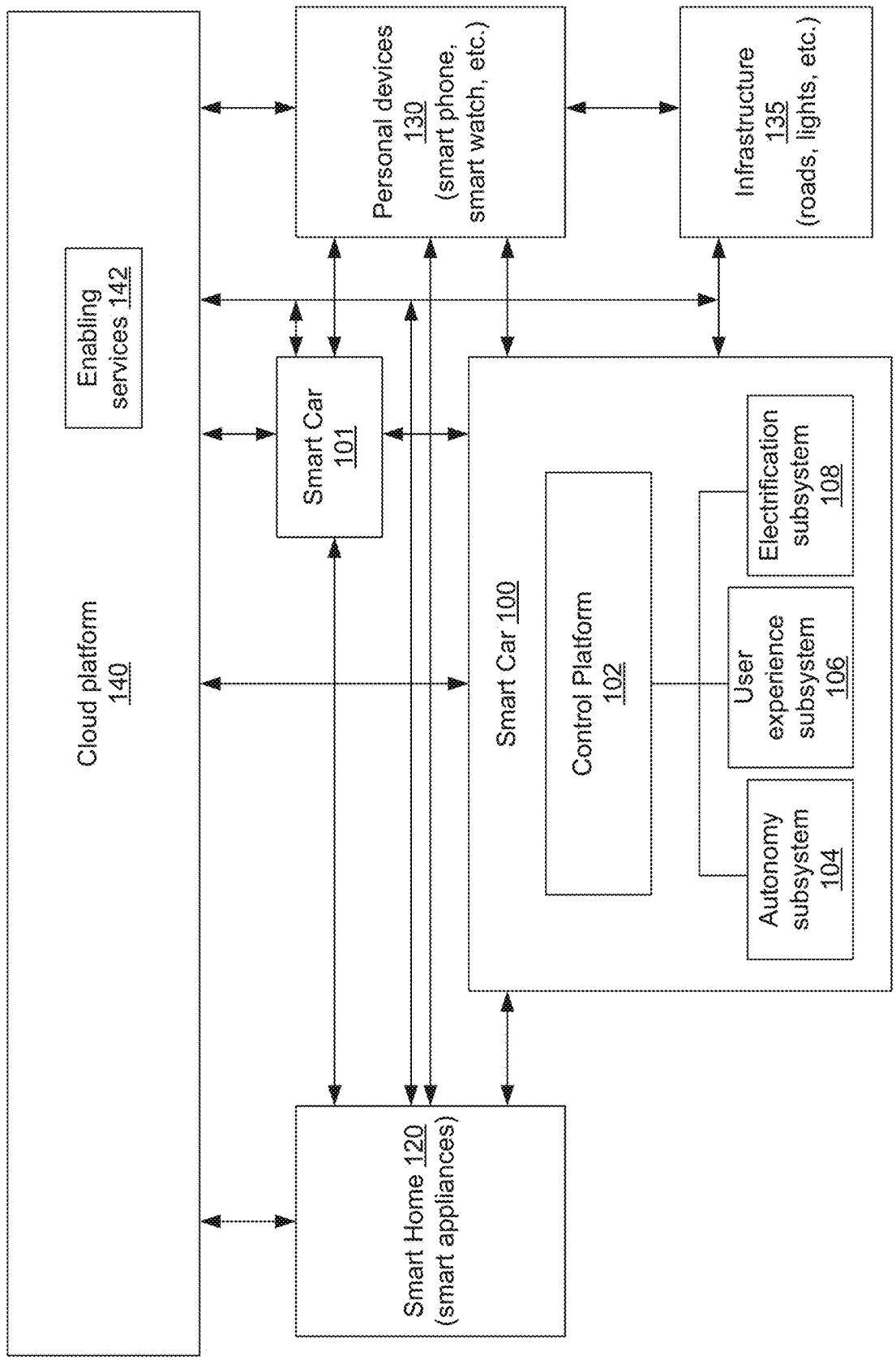
FIG. 1A is an illustration of a smart car interfacing with various entities, in accordance with an embodiment of the disclosure.

The present embodiments should not be construed as being limited to the descriptions set forth herein. Rather, these embodiments are provided as examples so that this disclosure will be thorough and complete and will fully convey the concept of the present embodiments to one of ordinary skill in the art. The appended claims illustrate some of the embodiments of the present disclosure.

While various references are made in this disclosure to "vehicles," "cars," etc. for the sake of brevity and ease of explanation, it should be understood that the present disclosure can apply to any man-made object, whether mobile or not. These objects may comprise, for example, vehicles that travel on a surface or through various media, including land, water, air, and space, whether with drivers in the vehicles or not. These objects may also be, for example, stationary objects that may be used for controlling/providing guidance for other mobile vehicles. These objects/vehicles are not limited to use on Earth, but may also be used on extra-terrestrial objects (planets, moons, asteroids, etc.). These objects/vehicles may also be referred to as "smart machines." Since it will be tedious to name all places that these smart machines can travel, it should be understood that various embodiments of the disclosure are not limited to specific locales listed.

Like reference numerals refer to like elements throughout the specification. All terms including descriptive or technical terms used herein should be construed as having meanings that are obvious to one of ordinary skill in the art. When a term has an ambiguous meaning due to evolving of language, precedent cases, or the appearance of new technologies, the meaning of a term used in this disclosure should first be clarified by its usage and/or definition in this disclosure. The term should then be clarified as one of ordinary skill in the art would have understood the term at the time of this disclosure.

When a part "includes" or "comprises" an element, unless there is a particular description contrary thereto, the part can further include other elements. The term "unit" in the embodiments of the present disclosure means a software component or a hardware component that performs a specific function. The hardware component may include, for example, a field-programmable gate array (FPGA) or an application-specific integrated circuit (ASIC).

Software, or software component, may refer to executable code and/or data used by the executable code in an addressable storage medium. Thus, software may be, for example, object-oriented software components, class components, and task components, and may include processes, functions, attributes, procedures, subroutines, segments of program code, drivers, firmware, application programs, micro codes/circuits, data, a database, data structures, tables, arrays, or variables.

A function provided by a "unit" may be divided into additional components and "units."

Reference will now be made in detail to embodiments, examples of which are illustrated in the accompanying drawings. In this regard, the present embodiments may have different forms and should not be construed as being limited to the descriptions set forth herein.

In the following description, well-known functions or constructions are not described in detail so as not to obscure the embodiments with unnecessary detail.

FIG. 1A is an illustration of a smart car interfacing with various entities, in accordance with an embodiment of the disclosure. Referring to FIG. 1A, there are shown a plurality of smart cars 100 and 101, a smart home 120, personal devices 130, infrastructure 135, and a cloud platform 140. In this example, there is shown for the smart car 100 a control platform 102 that communicates to the autonomy subsystem 104, the user experience subsystem 106, the electrification subsystem 108, and the sensors 110. The cloud platform 140 comprises enabling services 142. The smart car 101 may be similar to the smart car 100, or it may have different capabilities due to different manufacturer and/or options.

The control platform 102 receives feedback data and status from various sensors in the smart car 100. The control platform 102 may process the myriad of feedback data and status and provide appropriate control commands to various vehicle subsystems to keep the smart car operating as desired. For example, the control platform 102 may send commands to the autonomy subsystem 104 to keep an appropriate speed and to keep the vehicle in the desired part of the road. The control platform 102 may send commands to the user experience subsystem 106 to control the radio by tuning it to stations that are of interest to the driver as the present station's signal starts to fade, and to turn on heat/AC as appropriate to keep the interior of the car at a temperature designated by the driver. The control platform 102 may send commands to the electrification subsystem 108 to use battery power to assist the engine for hybrid cars, to manage battery cells, etc.

The smart car 100 may also be in communication with the smart home 120. For example, as the smart car 100 nears the smart home 120 of the driver, the smart home 120 may open the garage door and turn on the lights. The smart car 100 may also be in communication with the personal devices 130 owned by the driver. The personal devices 130 may be, for example, a smart phone or a smart watch. With such personal devices 130, the driver may be able to unlock the smart car 100 as he gets near, and turn on the smart car 100 and turn on the heater/AC if he wants to have the car in a comfortable state when he gets to it. The communication between the smart car 100 and the personal devices 130 may happen automatically when the driver approaches the smart car 100.

The smart car 100 may also be in communication with the infrastructure 135. The infrastructure 135 may comprise the various roads that the smart car 100 can travel on, as well as street lights, signal lights, etc. The infrastructure 135 may gather information from various parts of the infrastructure 135, smarts cars including the smart cars 100 and 101, smart home 120, and the personal devices 130 to better coordinate traffic flow. For example, if the infrastructure 135 anticipates congestion, it can alert other entities so they can re-route themselves. In some cases, the infrastructure 135 may suggest alternate routes to one or more of the smart cars on the road to relieve traffic congestion.

The infrastructure 135 may reserve certain roadway paths just for autonomous vehicles at certain times of day, and the reserved pathways may be changed in real time to optimize traffic flow. The traffic management by the infrastructure 135 may be due to inputs from various sensors that are part of the infrastructure (cameras, radar, etc.), input from various emergency response centers (police, fire department, ambulance services, etc.) as well as from inputs from the other entities such as the smart cars 100 and 101, the smart home 120, and the personal devices 130. The infrastructure 135 may also take into account historical data for traffic, current events (sport, concerts, conferences, etc.) that may lead to additional traffic for the event goers.

Additionally, the smart cars 100 and 101, the smart home 120, the personal devices 130, and the infrastructure 135 can communicate with each other via the cloud platform 140 as well as directly with each other to provide better services to a user by aggregating data. One example could be with infotainment where the user can be streaming media content via an appliance in the smart home 120. When the user gets in the smart car 100, the smart car 100 can continue to play the same media content from the infotainment system in the smart car 100. And similarly, when the user leaves his smart home 120 or his smart car 100, the personal device 130 can continue playing the media content. Another example could be a shopping service that aggregates in the cloud platform 140 the items that should be included in a user's shopping list, and sends recommendations to the navigation system in the smart car 100 to a store near the present route, and then once at the store, the personal device 130 guides the user to the items, checks the items as they are picked, and/or pays for the items.

The smart car 100 may also be in communication with other smart cars, such as the smart car 101. The smart car 100 can communicate directly to the smart car 101 or communicate via the cloud platform 140 to exchange information and/or share resources. For example, the smart car 100 may share its trajectory model including its speed, position, and other parameters with other smart cars to help improve efficiency for all smart cars. In some cases, the information desired from other smart cars may be from sensors that are not available to the present smart car, or for areas that are not directly visible to the present smart car.

For example, the smart car 100 may have entered a curve and detected an oncoming wide vehicle that is in the curve or about to enter the curve. This information can be marked as urgent and sent to nearby cars for real time use. Accordingly, the smart car 101 following behind the smart car 100 may take appropriate actions such as edge away from the center line or slow down to allow the wide vehicle to come out of the curve, etc. The wide vehicle itself may also send information about itself to nearby vehicles. Or, there might be a disabled car on a shoulder of the curve and this information might be marked as urgent for nearby cars, but also uploaded to the cloud platform 140 for other vehicles to use at a later time. The later coming vehicles that near the curve can then access the cloud platform 140 for information about its path ahead.

Smart cars may also share information about nearby non-smart cars so that additional sensors or sensing time may be dedicated to these cars since their behavior may be considered to be unknown or unpredictable. The communication between the smart cars will allow each smart car to be able to further improve the environment mapping for itself.

Other examples of communication with the smart car 100 may be, for example, the personal device 130 (smartphone or smartwatch, for example) that may alert nearby smart cars 100 and 101 to the pedestrian/bicyclist/etc. who is the owner of the personal device 130. Accordingly, the smart cars 100 and 101 may be able to have a more detailed environment map. A child may also have a personal device 130 that he can wear as a bracelet or a necklace to alert the smart cars 100 and 101. It is also conceivable that a pet can be equipped with personal devices 130 in its collar or embedded in its body.

Accordingly, any moving/movable object may have a personal device/beacon that can alert smart cars. Additionally, a non-movable object can also warn of danger. For example, the smart home 120 may keep track of a child/pet and may alert passing cars to the child/pet, or a guardrail at the edge of a ravine can warn the smart cars 100 and 101, and hence the drivers if the drivers are involved in driving.

This communication between smart cars, between a smart car and a smart home, or between a smart car and a personal device 130, which as can be seen, can include simple beacons as well as smartphones and smart watches, may be direct, or indirect through the cloud platform 140, or indirect through other smart car(s) and/or personal devices 130.

While some examples of communication for the benefit of a smart car have been mentioned, various embodiments of the disclosure can also be used for other devices or benefits. For example, a pedestrian/bicyclist/etc. can be warned of nearby traffic/obstacles/dangers via a personal device 130. Or a smart device platform (smart car, personal device, etc.) can also be used to control street lights, to locate parking spots or parking meters. For example, a street light may be dimmed or turned off until it is alerted by a smart car moving within range, and brightens itself. The street light may detect a smart device (smart car, personal device, etc.) and turn on the light. The street light may also detect something else on the street/sidewalk using one or more sensors (radar, camera, etc.) and determine that brighter lighting is needed. For example, if a small animal is detected on the street with no other vehicles (cars, motorcycles, bicycles, etc.) nearby, the street light may determine that its light need not be brightened. However, if a human shape is detected, the street light may brighten itself, as well as map the human shape in its environment map to be shared with nearby devices. This may include smart homes so that the smart home can update its environment map. The smart home 120, for example, may keep track of nearby vehicles/people for various purposes including detection of possible break-in to the smart home 120. Accordingly, the smart home 120 may also be a generic reference to a business or other commercial property.

The smart car 100 may also locate parking spots in a parking lot or with a parking meter by either communicating with the parking meter, parking infrastructure, and/or the cloud platform 140 to locate available spots. The smart car 100 may also be able to pay the parking meter or the parking spot using a pre-arranged payment system such as, for example, Samsung Pay. The payment may be made for an estimated time entered by the driver of the smart car, or may be made periodically (once per hour, for example).

The guardrail, the streetlight, the parking meter, and the parking lot may be considered to be part of the infrastructure 135 in some cases. However, various embodiments may add or leave out different entities (e.g., leave out private parking lots) as part of the infrastructure 135.

Another example may be when a smart car informs other smart cars that it is braking or anticipates braking. This may be useful, for example, if several cars are traveling in a line so that cars behind the lead car cannot sense the obstacle. In this situation, all cars behind the lead car can then know of intent by the lead car to brake due to an obstacle that the following cars cannot sense, and they can all brake at the same time.

Information may also be stored in the cloud platform 140 and pulled by the smart car 101 as needed if it determines that it does not need real time data immediately. That information may have been uploaded by various users of the road and/or by the infrastructure 135. Accordingly, the smart car 100 can pull data for conditions of the road as it nears that location. Another example could be, in case of any failure in a part of a system for the smart car 100, other smart cars such as the smart car 101 could help by sharing their resources. Therefore, if some sensors of the smart car 100 become inoperative, the smart car 100 may be able to get environment information regarding other cars, obstacles, road conditions, etc. to be able to keep driving safely, whether in an autonomous mode or in a lesser capacity in assisting the human driver.

Another example may be when the smart car 100 can make available its infotainment content of books, songs, movies, games, environment mapping, etc. to other smart cars directly or via the cloud platform 140. The smart car 101 may be able to stream or download for later playback, for example, a movie for people in the car, including the driver if the smart car 101 is driving autonomously.

Infotainment content in the smart car 100 may be advertised, for example, via the cloud platform 140 or via broadcast messages that can be discovered and understood by surrounding vehicles. This could potentially allow for the resale of content across vehicles in the context of a mobile datacenter in the vehicle platform such as the smart car 100. The vehicle platform may be able to cache content to nearby cooperative devices, vehicles, and/or premises to leverage future known locations/times of where the vehicle platform will be operating. The content caching to nearby device/vehicle/premise may also depend on the interest shown by any of those entities in the content. This may allow for "meshed" distribution of data that can reduce traffic to and from the cloud platform 140.

Accordingly, as explained above, and as will be explained further later, a platform is provided for various vehicles, including the smart cars 100 and 101, to facilitate sensing/perceiving, analyzing, and reacting/performing. The inputs for sensing/perceiving are provided by the various sensors in a smart car 100 or 101, from a driver/passenger of the smart car 100 or 101, from other smart cars, and/or from data from a cloud platform such as the cloud platform 140. The reacting/performing may allow controlling one or more functions of a vehicle such as the smart car 100 or 101.

Also, in cases where a software driver running on any system on chip (SoC) or coprocessor fails, the hypervisor software may be able to trigger execution of similar software drivers running under another hypervisor running on a different processor. This may provide, for example, software redundancy for operating sensors. There may also be a plurality of sensors of the same type to provide hardware redundancy. Additionally, there may be similar software and hardware redundancy for various parts of the smart car 100, including for processors.

As described, the smart car 100 may sense other cars via its sensors, as well as directly communicate with other smart cars for various information. It should be realized that these are only a few examples, and various embodiments of the disclosure are not limited by or to these examples.

Figure 1B:
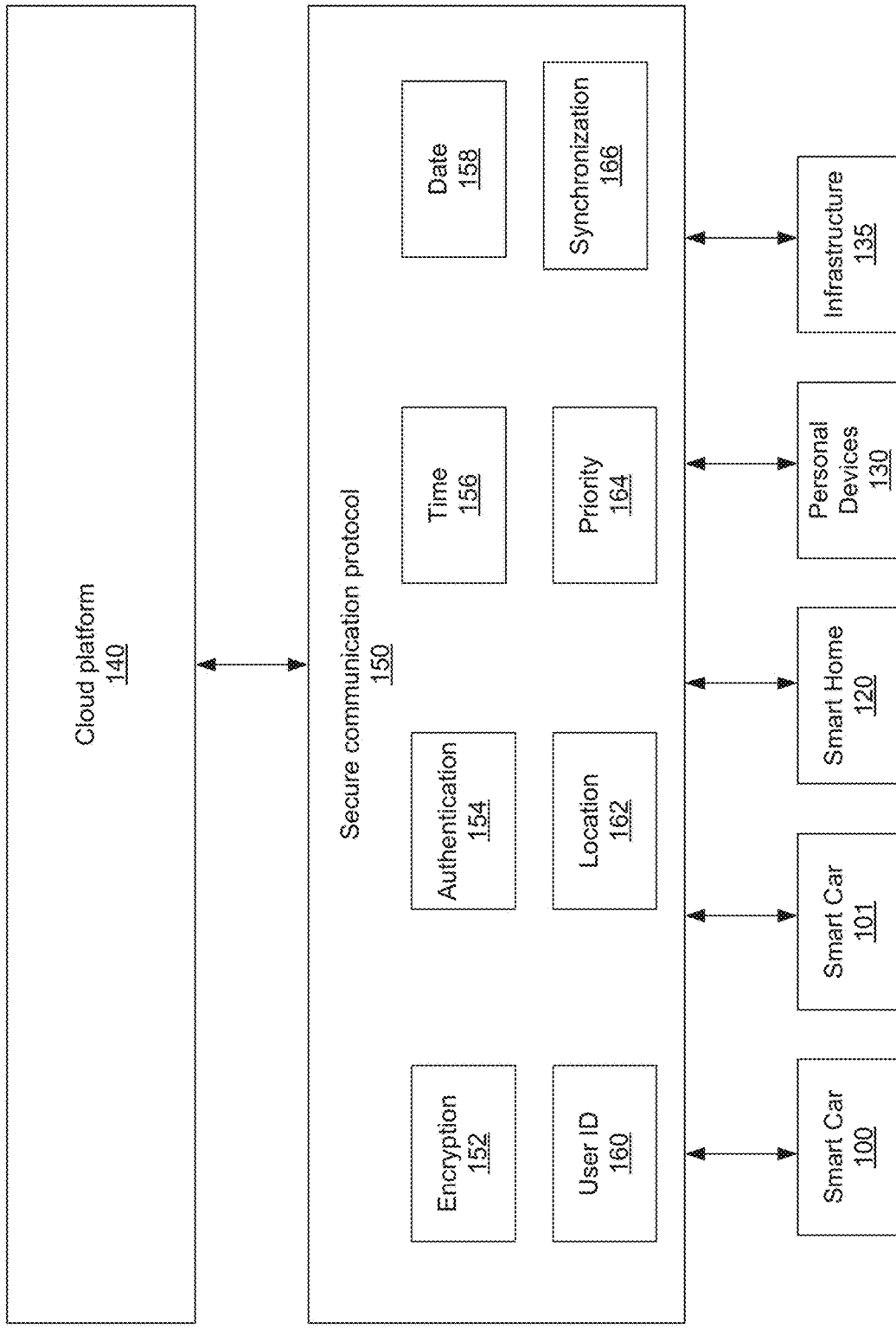
FIG. 1B is an illustration of a protocol for a smart car interfacing with various entities, in accordance with an embodiment of the disclosure.

FIG. 1B is an illustration of a protocol for a smart car interfacing with various entities, in accordance with an embodiment of the disclosure. Referring to FIG. 1B, there are shown the smart cars 100 and 101, the smart home 120, the personal devices 130, the infrastructure 135 and the cloud platform 140 that are substantially as described in FIG. 1A. There is also shown the secure communication protocol 150. When communicating between the smart car 100 and any other entity, including another smart car 101, the smart home 120, the personal devices 130, the infrastructure 135, and the cloud platform 140, the secure communication protocol 150 may be used. The secure communication protocol 150 may comprise in part transmitting one or more of various information such as, for example, the time 156, the date 158, the user ID 160, and location 162 to keep track of communication, and also to select specific entities with which to share information.

For example, trajectory data for the smart car 100 may be shared with other smart cars, emergency vehicles, and/or supervising devices related to the infrastructure 135 such as, for example, for traffic control. There may also be a priority 164 sent as well as synchronization data 166. The priority 164 may be, for example, for emergency information that may need to take priority over all other communication. An example may be an emergency vehicle that needs to clear its path and so sends a top priority signal to other smart vehicles to signal them to move out of the way and slow down. A low priority communication may be, for example, uploading or downloading a media file.

Any communication may be encrypted using the encryption 152, and authenticated using the authentication 154. Encryption may be use dependent. For example, transferring private media from the owner of the smart car 100 to the owner's personal device 130 may not require encryption. However, that can also be an option by the user. Some data transfer, however, may need to be encrypted and authenticated. That may be, for example, any firmware update over the air for the smart car 100.

The synchronization data 166 may be used for any synchronization that may be desired by the smart car 100 and any other device/entity. For example, the time 156 and the date 158 may be synchronized at various times to compensate for clock drift and/or various time zones, location may be synchronized to ensure that the geo-location system is accurate, etc. The synchronization data 166 may also be used for encryption 152 and/or authentication 154 when the encryption and/or authentication process changes periodically.

The synchronization data 166 may also be exchanged between the smart car 100 and another device, such as, for example, the smart car 101, the smart home 120, the personal device(s) 130, and the cloud platform 140. The exchange of synchronization data 166 may ensure that, when desired, a connection between the smart car 100 and the other device may remain open even during periods when no other data is communicated between the smart car 100 and the other device. While a connection was mentioned between the smart car 100 and another device, various embodiments of the disclosure may allow a connection between any two devices that support the illustrated protocol, including the synchronization data 166.

While some aspects of the secure communication protocol 150 have been generally described, various embodiments may use different schemes. Accordingly, the specific parts described do not limit any embodiment of the disclosure.

Figure 1C:
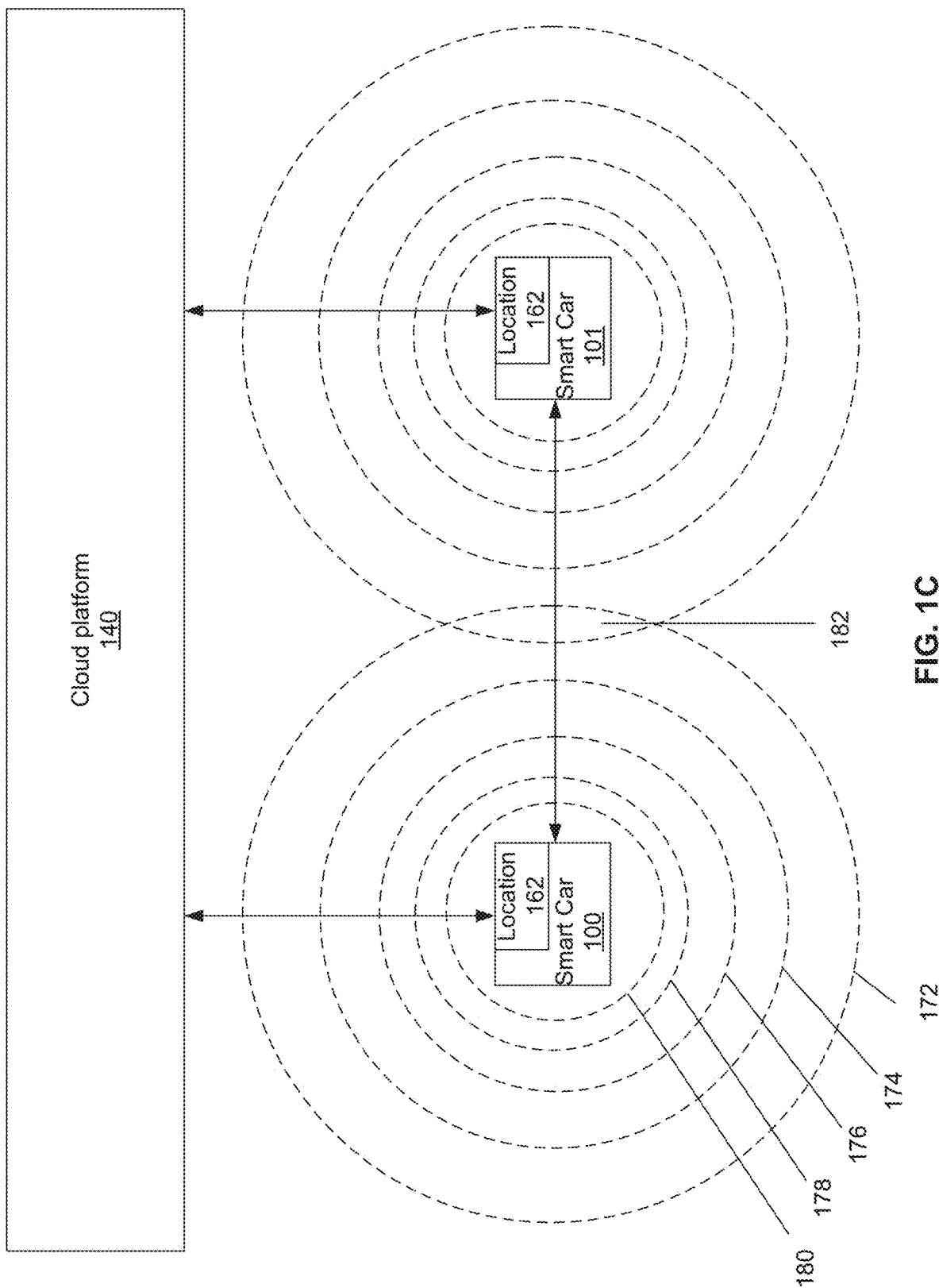
FIG. 1C is an illustration of a collision avoidance scheme, in accordance with an embodiment of the disclosure.

FIG. 1C is an illustration of a collision avoidance scheme, in accordance with an embodiment of the disclosure. Referring to FIG. 1C, there are shown smart cars 100 and 101, with each smart car having a safety cushion zones 172, 174, 176, 178, and 180. Each safety cushion zone may be determined by the smart car depending on its speed and environment conditions (weather, road, traffic, types of vehicles in the environment, etc.). As each safety cushion zone 172, 174, 176, 178, and 180 is breached, the smart car 100 (or 101) may take corrective action to regain its safety zones for collision avoidance.

For example, when the outermost safety cushion zone 172 is breached, the smart car 100 may devote more time and resources to monitoring the breaching smart car 101. When the next safety cushion zone 174 is breached, the smart car 100 may communicate a warning to the smart car 101 that it is coming too close in addition to further monitoring. When the next safety cushion zone 176 is breached, the smart car 100 may start to take active measures to regain safety cushion in addition to the previous measures taken. When the next safety cushion zone 178 is breached, the smart car 100 may take more drastic measures including swerving away if possible, braking or accelerating harder as necessary, in addition to the previous measures taken. When the last safety cushion zone 180 is breached, the smart car may prepare for collision if it seems inevitable by getting ready to deploy various safety devices including air bags and tensing the safety restraints, in addition to the previous measures taken. The smart car 100 may also prepare to call for help in the event of an accident.

The smart car 100 may also inform the infrastructure 135 at various points so that the infrastructure 135 can take that into account for possible traffic flow disruption. Accordingly, the infrastructure 135 may stop and disable the smart car 101 (if it is able to) if it determines that the smart car 101 has been driving unsafely for a period of time. Or, if the smart car 101 is not able to be stopped (it is not a smart car), police may be informed by the infrastructure 135.

This is just one example of possible steps that can be taken. The number of safety cushion zones may also vary, and different steps may be taken for breaching of each safety cushion zone. Additionally, the breaching of a safety cushion zone may be determined by different methods. For example, a safety cushion zone may be breached by a physical object such as the smart car 101, or the safety cushion zones of the respective smart cars 100 and 101 may intersect as shown by the collision avoidance envelope 182.

The collision avoidance envelope 182 may be determined by, for example, the smart car 100 accessing the cloud platform for information for neighboring cars such as the smart car 101. Part of the information may be the location 162 and/or the safety cushion zones of the smart car 101. This information may also be directly communicated between the smart cars 100 and 101. Accordingly, various smart cars may provide its trajectory (speed, direction, location, etc.) to the cloud platform 140 as well as directly to a neighboring smart car, and possibly to the infrastructure 135. Additionally, the smart car 100 may advertise its short term intent to the cloud platform 140 and/or a neighboring smart car 101, and possibly to the infrastructure 135. The short term intent may be such things as, for example, changing lanes, turning, entering/exiting a highway, slowing down, speeding up, etc. Various embodiments may also advertise longer term intent such as, for example, part of its upcoming route.

While various embodiments have been described for communication between smart cars, a smart car 100 may also take into account a non-smart car with a collision avoidance strategy/tactics that takes into account the relative unpredictability of the non-smart car since the intent of the non-smart car is unknown. This may include providing a little more buffer space to the smart car, devoting more sensors/processing for the non-smart car, etc.

If the driver is driving the smart car 100, breaching of the various safety cushion zones may result in the smart car 100 taking active measures by controlling the smart car 100 to increasing extents if the driver of the smart car 100 is not responding appropriately (moving away, braking, accelerating, etc.).

A personal device 130 may also be used for guidance for a smart car. This may occur, for example, if some portion of the smart car 100 is out of service. However, if there is enough functionality in the smart car 100 to be able to receive and process information from the personal device 130, the smart car 100 may be able to use the additional input from the personal device 130 to augment its remaining sensors. For example, the personal device 130 may provide video input for a specific direction, or be able to connect to other smart cars or platforms for environment map and/or other information. Even if the smart car 100 is wholly operational, the personal device 130 may be able to provide some input that the smart car 100 does not have. This may be due to further advances for the personal device 130.

Figure 1D:
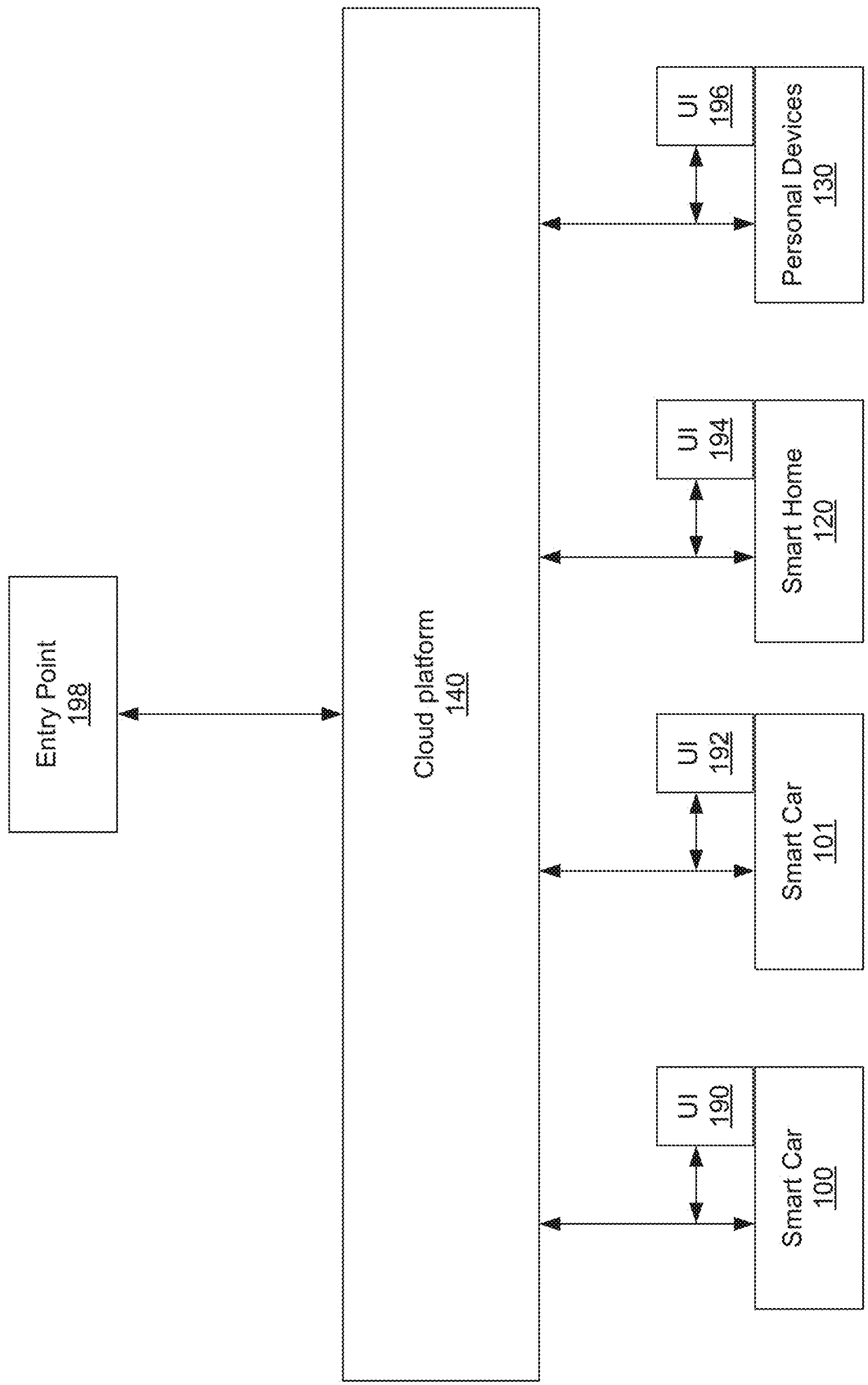
FIG. 1D is an illustration of further communication to and among smart cars, smart home, and smart mobile devices, in accordance with an embodiment of the disclosure.

FIG. 1D is an illustration of further communication to and among smart cars, smart home, and smart mobile devices, in accordance with an embodiment of the disclosure. Referring to FIG. 1D, there are shown the smart cars 100 and 101, the smart home 120, and the personal devices 130. The smart car 100 may have a user interface 190, the smart car 101 may have a user interface 192, the smart home 120 may have a user interface 194, and the personal device 130 may have a user interface 196. The user interfaces 190, 192, 194, and 196 may be similar to offer a consistent user experience. The user interfaces 190 and 192 may be either built in to the smart cars 100 and 101, or may be dedicated after-market devices. The smart cars 100 and 101 may also use other electronic devices such as a laptop, tablet, or smartphones as a user interface, similarly to the user interface 196 that is provided by a software application running on the personal device 130.

The smart home 120 may also have one or more user interfaces 194 that are built in to the various appliances. Alternatively, the user interfaces may also be dedicated after-market user interfaces and/or the user interface application for a personal device as described for the smart cars 100 and 101. The user interface 196 for the personal devices 130 may be a software application. While the input and output to the user interfaces may differ if the hardware portion of the user interfaces is different, similar hardware can have similar displays, menus, etc. for continuity among the various devices.

For example, smart cars 100 and 101 with built-in user interfaces as well as after-market devices may all be similar in that they have a touch screen and may also understand voice commands. This may also be true of various personal devices 130 that have touch screens such as laptops and smart phones.

There is also shown an entry point 198 that may be used to access information of the various smart cars 100 and 101, smart home 120, and personal devices 130. The information, which may be accessed using the protocol described in FIG. 1B such as encryption and authentication, may be accessed via a web page by any device that can connect to the Internet, either wirelessly or via a wired connection. The device can be used to log on to the entry point using, for example, a login name and password, and the login process may be a simple login, or require verification in addition to the login name and password. The information may comprise, for example, various operational data for the smart cars 100 and 101 to aid in maintaining the car by a mechanic or owner. The owner or mechanic may also receive the engine status data as well as be able to reset the check engine light for the smart car 100/101. The information may be received from, for example, the cloud platform 140 via the entry point 198.

The entry point may also be used to control a smart car 100 or 101 to a certain extent. For example, a law enforcement official may be able to send commands to bring the smart car 100 to a safe stop, and then turn off the engine. Or the owner may command the car to honk its horn and/or flash its lights to allow the owner to find the car in a parking lot.

The entry point 198 can also be used to control the smart home 120 as well as the personal devices 130 via the cloud platform 140.

Figure 2:
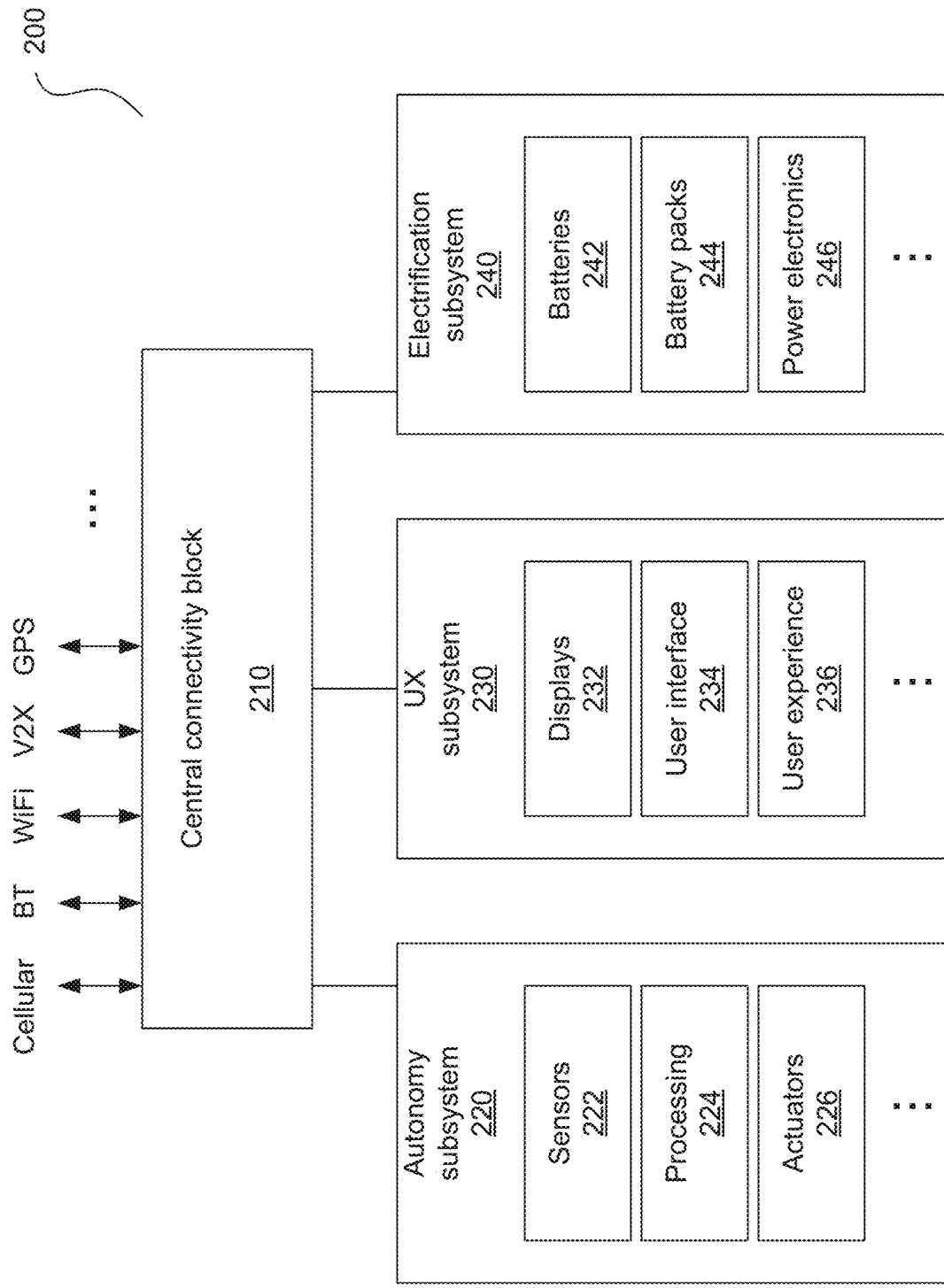
FIG. 2 is a high level view of a centralized architecture of a vehicle, in accordance with an embodiment of the disclosure.

FIG. 2 is a high level view of a centralized architecture of a vehicle, in accordance with an embodiment of the disclosure. Referring to FIG. 2, there is shown an abstraction of a vehicle 200 that may be similar to the smart car 100. The vehicle 200 comprises a central connectivity block 210 that communicates with the autonomy subsystem 220, the user experience subsystem 230, and the electrification subsystem 240. The central connectivity block 210 may also be able to communicate to external devices as well as devices carried by the driver and/or passengers. The communication may be via a number of different protocols and technologies such as, for example, using cellular communication, WiFi, V2X, Bluetooth, etc. The central connectivity block 210 may also receive GPS signals (and/or other similar satellite location signals) to be able to determine its location.

The central connectivity block 210 can communicate with the autonomy subsystem 220 to receive data from the sensors 222. This data may be processed by the central connectivity block 210 and commands sent to various actuators 226 to keep the vehicle 200 on course. The commands may also be sent to the processing unit 224 for processing to lower level signals to control the actuators 226.

The central connectivity block 210 can communicate with the user experience subsystem 230 to ensure that the driver/passenger(s) are comfortable. For example, the central connectivity block 210 may output directions and/or information for the driver/passenger(s) as needed on the displays 232. There may be directions/options for adjusting the interior temperature, lighting, choice of media (for example, broadcast/satellite television or radio, Internet, connect to a personal device), etc. The displays 232 may also comprise various lights/LEDs and devices that give audio or vibrational alerts.

The user interface 234 may include input devices, which may include a touch screen on one or more of the displays 232. Other types of input devices can include microphone, buttons, dials, switches, and cameras. The user interface 234 can be used to enter commands and/or choices. A camera may, for example, track the face or eyes of the driver to give further information. For example, if a camera sees the driver/passenger look to a display screen when a song is playing, information about the song (such as the song name and singer) may be displayed or given verbally.

The user experience block 236 can be used to generally make interaction between a driver/passenger and the vehicle 200 safer, smoother, and more pleasant. An infotainment system can be connected to various safety and control features of the vehicle 200 to provide alerts to, for example, the driver if the driver is on a collision course with an obstacle or another vehicle, or seems to be leaving its lane unintentionally. One way may be to infer choices for the user based on previous choices. For example, if a radio station starts to fade as it is left behind, the user experience block 236 can look for a similar station within range and tune to it. The user experience block 236 may also track previous selections for temperature, and based on outside conditions automatically turn on and/or adjust temperature, air from the outside, and air conditioning (AC).

The electrification subsystem 240 may be used to monitor and control the conditions of various electrical parts of a vehicle. For example, the batteries 242 can be monitored to ensure that the cells are in good condition for charging and discharging. The battery packs 244 can be monitored to ensure that the overall battery pack can be charged properly and provides enough power as needed. The power electronics 246 may be the parts that are involved in converting mechanical energy to electricity to charge the battery/battery pack and for converting electrical energy to mechanical energy, as well as providing electrical energy to various electrical components for their operation.

It should be noted that only some functional blocks for a vehicle have been described as examples and some examples are provided for each of these functional blocks for illustration purposes. The disclosure is not limited to or by these descriptions.

Figure 3:
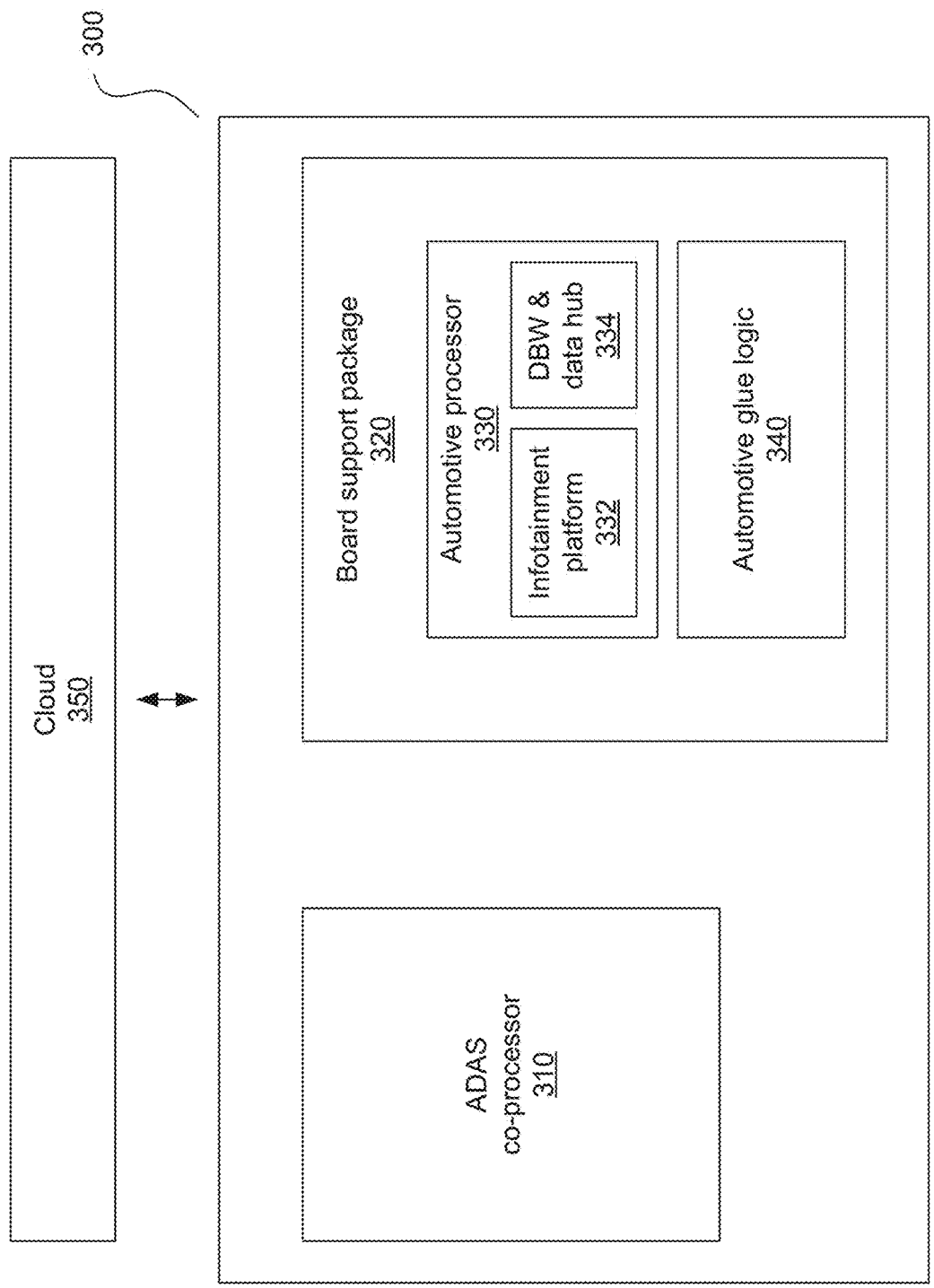
FIG. 3 is a high level block diagram of automotive processors for controlling a vehicle, in accordance with an embodiment of the disclosure.

FIG. 3 is a high level block diagram of automotive processors for controlling a vehicle, in accordance with an embodiment of the disclosure. Referring to FIG. 3, there are shown the processor block 300 and the cloud 350. The processor block 300 may communicate with the cloud 350 to store various vehicle specific information as well as environment information around the vehicle. The vehicle specific information may be private and protected from access by others, while the environment information may be accessed by others. The environment information may comprise, for example, road conditions and lane closures, accidents, traffic conditions, etc. A vehicle will have many more processors or electronic control units (ECUs), and FIG. 3 shows one example of a simplified architecture. A processor is not limited to any specific type by function or name. For example, a processor can be a microprocessor, a controller, a microcontroller, an ECU, a CPU, a graphics processor (GPU), a digital signal processor, etc. The processor may be implemented by different technologies, such as, for example, custom chip, semi-custom chip, FPGA, etc. A processor may be, for example, a real-time processor. Where an implementation comprises a plurality of processors, a processor may be referred to as a co-processor.

The advanced driver assist systems (ADAS) co-processor 310 is used for processing the data and controlling various aspects of driving a vehicle. Accordingly, the ADAS co-processor 310 may alert the driver and/or take over braking, steering, and/or acceleration to avoid collisions and accidents. Some functionalities may include automated lighting, adaptive cruise control, automated braking, incorporation of GPS/traffic warnings, connecting to smartphones, alerting the driver to other vehicles or obstacles (for example, in blind spots), and keeping the driver in the correct lane. These functionalities may be used for completely autonomous driving by vehicles.

The board support package 320 comprises an automotive processor 330 and automotive glue logic 340. The automotive processor 330 may comprise, for example, an infotainment platform 332 that may be similar to the user experience subsystem 106 or 230. The drive by wire (DBW) and data hub 334 may be similar to the autonomy subsystem 104 or 220.

The automotive glue logic 340 may comprise the various hardware (and/or software) that are needed to have the individual processors, including the ADAS co-processor 310, function correctly to help automate at least some parts of operating a vehicle.

Figure 4:
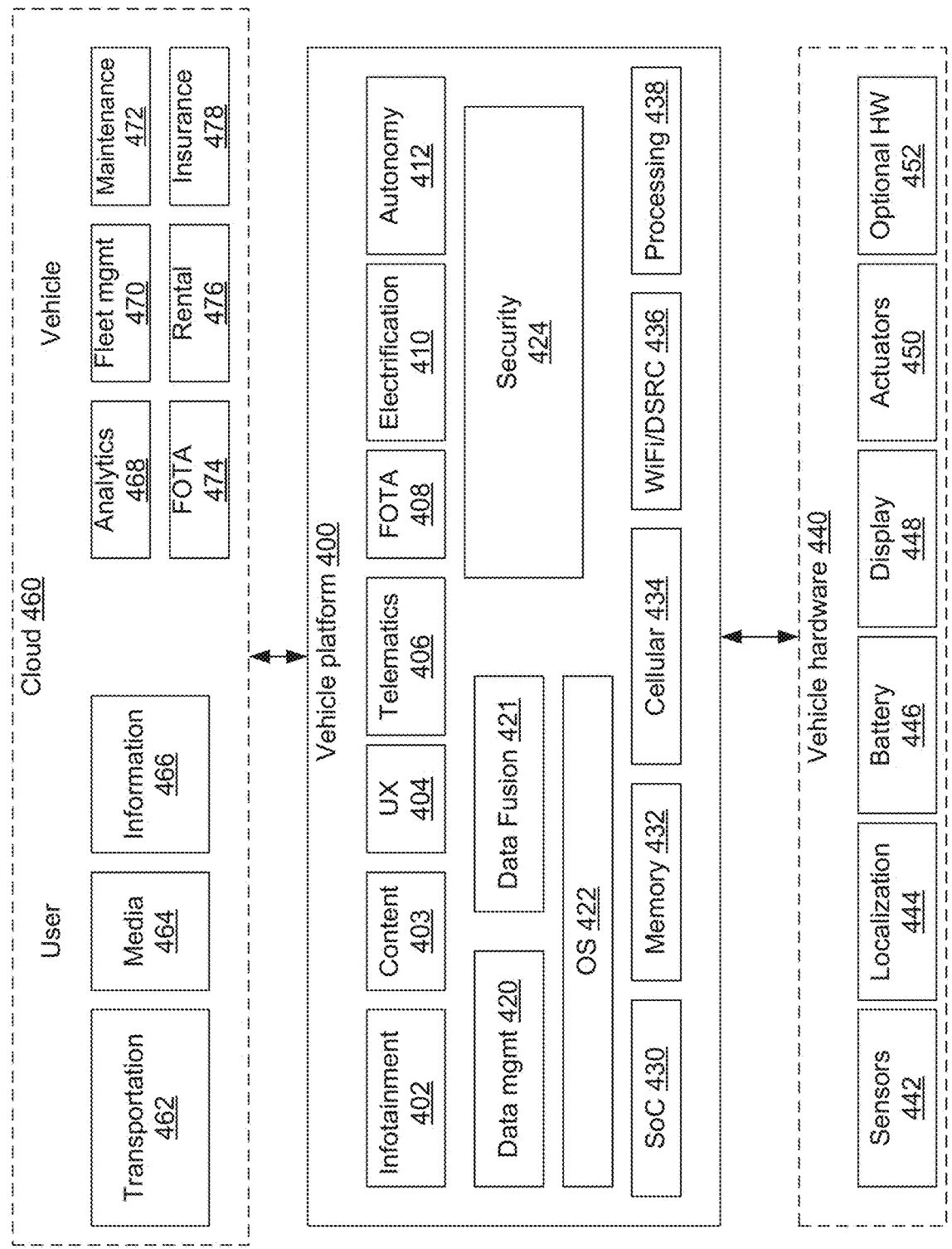
FIG. 4 is a block diagram of a vehicle platform, in accordance with an embodiment of the disclosure.

FIG. 4 is a block diagram of a vehicle platform, in accordance with an embodiment of the disclosure. Referring to FIG. 4, there is shown a vehicle platform 400 that communicates with various vehicle hardware components in the vehicle hardware block 440 and with the cloud 460 for various services. The vehicle platform 400 may be, for example, a part of the smart car 100. The vehicle platform 400 comprises application software layer for applications such as, for example, infotainment application 402, the user experience application 404, the telematics application 406, the firmware-update over the air (FOTA) application 408, the electrification application 410, and the autonomy application 412. While the FOTA application 408 specifies firmware, the FOTA application 408 may be generally used for updating any executable instructions/code in the smart car 100. The executable instructions/code comprise software, firmware, applications, etc. These applications work at the top layer and interface with various parts of the smart car 100 and its driver/passengers, and also communicate to other devices external to the smart car 100.

The infotainment application 402, the user experience application 404, the electrification application 410, and the autonomy application 412 have been described above. The telematics application 406 may allow communication with external devices to transmit and receive various types of data relating to the smart car 100. The telematics application 406 may also comprise or work in conjunction with other applications to provide for, for example, emergency warning system for the smart car 100, using GPS navigation, allowing use of integrated hands-free cell phones, wireless safety communications, and ADAS.

The FOTA application 408 can allow updates for many software modules in the smart car 100 to be received via wireless transmission. While some updates may need to be done while the smart car 100 is parked, other updates may be performed while the car is in operation. For example, minor updates for software that is not directly involved in operation or safety of the car may be updated while the smart car 100 is in motion. An example may be software for sound control for the infotainment system such as equalization control for music/voice playback. Additionally, updates may be made via, for example, connecting to various personal devices 130 that are able to connect to the Internet and/or to the cloud 460. Similarly, updates may be made to various personal devices 130 and/or to various smart appliances in the smart home 120 via the FOTA application 408 in the smart car 100. Accordingly, an entity may be updated by using an FOTA application of another entity and/or having an entity's FOTA application update another entity. While a single FOTA application 408 is shown, there may be a plurality of FOTA applications that may be used for different functionalities.

Below the application software layer is the control system layer. The control system layer may comprise the data management module 420, the data fusion module 421, the operating system 422, and the security module 424. The data management module 420 may receive data from various devices including hardware devices and sensors of the smart car 100 as well as from various software modules and applications of the smart car 100. The received data, which may be analyzed and/or processed as necessary, can then be stored in a database for other processors and/or ECUs to access. The global database may be located in, for example, the memory block 432. Depending on the architecture and design, the data management module 420 may also send any of the information it receives, analyzes, and/or processes directly to a processor or an ECU.

The data fusion module 421 may analyze/process various retrieved data from the database and/or received data from the data management module 420 and generate a coherent output. The data fusion module 421 may take data originating from various sources to generate a composite data that can be used by various portions of the smart car 100. For example, the data fusion module 421 of the smart car 100 may receive data from various sources such as, for example, traffic information directly from other vehicles or from a cloud platform regarding traffic beyond sensor range of the smart car 100, radar information, lidar information, sonar information, and/or camera images regarding the environment around the smart car 100. The data fusion module 421 may then correlate the relevant portions of the data to generate, for example, a 3-D module of the environment around the smart car 100 so that the smart car 100 can navigate the environment safely, whether autonomously or by assisting the driver.

The operating system 422 provides a structure for the various software modules and applications. The security module 424 monitors data received by the smart car 100 as well as software in the smart car 100 to ensure security and integrity for the smart car 100.

The hardware layer may comprise, for example, the system on chip (SoC) 430, the memory block 432, the cellular communication block 434, wireless communication block 436, and the processing block 438. The SoC 430 comprises a processor such as, for example, the ADAS co-processor 310, as well as some of the support functionalities needed by a processor. Accordingly, the SoC 430 may also include memory, communication circuitry, and I/O interfaces. Various SoCs may include different functionalities.

The memory block 432 may comprise volatile and non-volatile memory, as well as mass storage mediums such as, for example, hard drives. The memory block 432 may include volatile and/or non-volatile memory, as well as mass storage units such as, for example, hard disk drives. The memory block can be used to store executable instructions and data for operation of the smart car 100, and/or data loaded by a driver/passenger such as, music, electronic books, videos, etc. The music, electronic books, videos, etc. can be played by the smart car 100 in the infotainment center under control of, for example, the infotainment application 402.

The cellular communication block 434 may comprise suitable circuitry for allowing the smart car 100 and the driver/passenger(s) to send/receive cellular calls, text, and browse/download/upload from the Internet using, for example, the LTE standard or other similar cellular technology. The cellular communication block 434 may also be backwards compatible to present and older cellular technology such as, for example, 4G, 3G or 2G, as well as compatibility with the 5G LTE standards. Future upgrades of the cellular communication block 434 may be made via the FOTA application 408. Similarly, any firmware for the smart car 100, including for sensors, actuators, SoC, co-processor, radio, localization, etc. may be made via the FOTA application 408.

The wireless communication block 436 may comprise various circuits for communicating via one or more of a number of wireless standards such as, for example, Bluetooth, WiFi, dedicated short-range communication (DSRC), near field communication (NFC), etc. The smart car 100 may act as an access point for various devices owned by the driver and/or the passenger(s).

The processing block 438 may comprise processors such as the ADAS co-processor 310, the automotive processor 330, as well as one or more of the numerous ECUs that are present in the smart car 100.

The vehicle platform 400 can communicate with the vehicle hardware block 440 using one or more of the communication circuits described above. The vehicle hardware block 440 may comprise, but is not limited to, sensors 442, localization block 444, battery 446, display 448, actuators 450, and optional hardware 452. The sensors 442 may comprise, for example, radar, lidar, sonar, and cameras. The sensors 442 can also include those that monitor the engine and other car components. For example, the sensors 442 include oil pressure sending unit, the coolant thermometer, the tire pressure sensor, voltmeter, and ammeter among other things.

The localization block 444 may be used to localize specific hardware that may be different from country to country or from region to region. For example, there may be different frequencies supported by the receivers and transmitters for the various wireless communications supported by the smart car 100. There may also be support for different types of satellite navigation receivers, beacons, etc. in different parts of the world.

The battery 446 may be used as a power source in assisting an engine for a hybrid car or as the sole power source for an electric car. There may also be a smaller battery for non-drivetrain uses such as headlights and tail lights, and accessories operation. The display 448 can be used to output data and status for the driver/passenger. The actuators 450 can be used to control the smart car 100. For example, the actuators 450 can include various electric motors for the wheels, for opening/closing the windows, for engaging the brakes, for providing the correct amount of fuel for the internal combustion engine, etc. The optional hardware 452 may be aftermarket hardware to replace hardware that came with the smart car 100 or to add to the functionality of the smart car 100.

The vehicle platform 400 can communicate with the cloud 460 for various services. Some of the services may be requested by the driver/passenger such as, for example, transportation 462, media 464, information 466, and some of the services may be requested by the vehicle such as, for example, analytics 468, fleet management 470, maintenance 472, FOTA 474, rental 476, and insurance 478. Accordingly, the driver/passenger may be able to search for and find information for a variety of things. Fleet management 470, for example, may be keeping track of various vehicles in the fleet in order to be able to use the fleet for maximum efficiency. The maintenance 472 may allow monitoring of the smart car 100 so as to be able to offer suggestions for maintenance and upkeep for the vehicle before more serious problems arise. When prompted, the smart car 100 may also be able to offer suggestions for repair shops in the area that are able to handle the type of maintenance needed.

While some descriptions were made, it should be noted that all possible details cannot be listed for a complex device like a car.

Figure 5A:
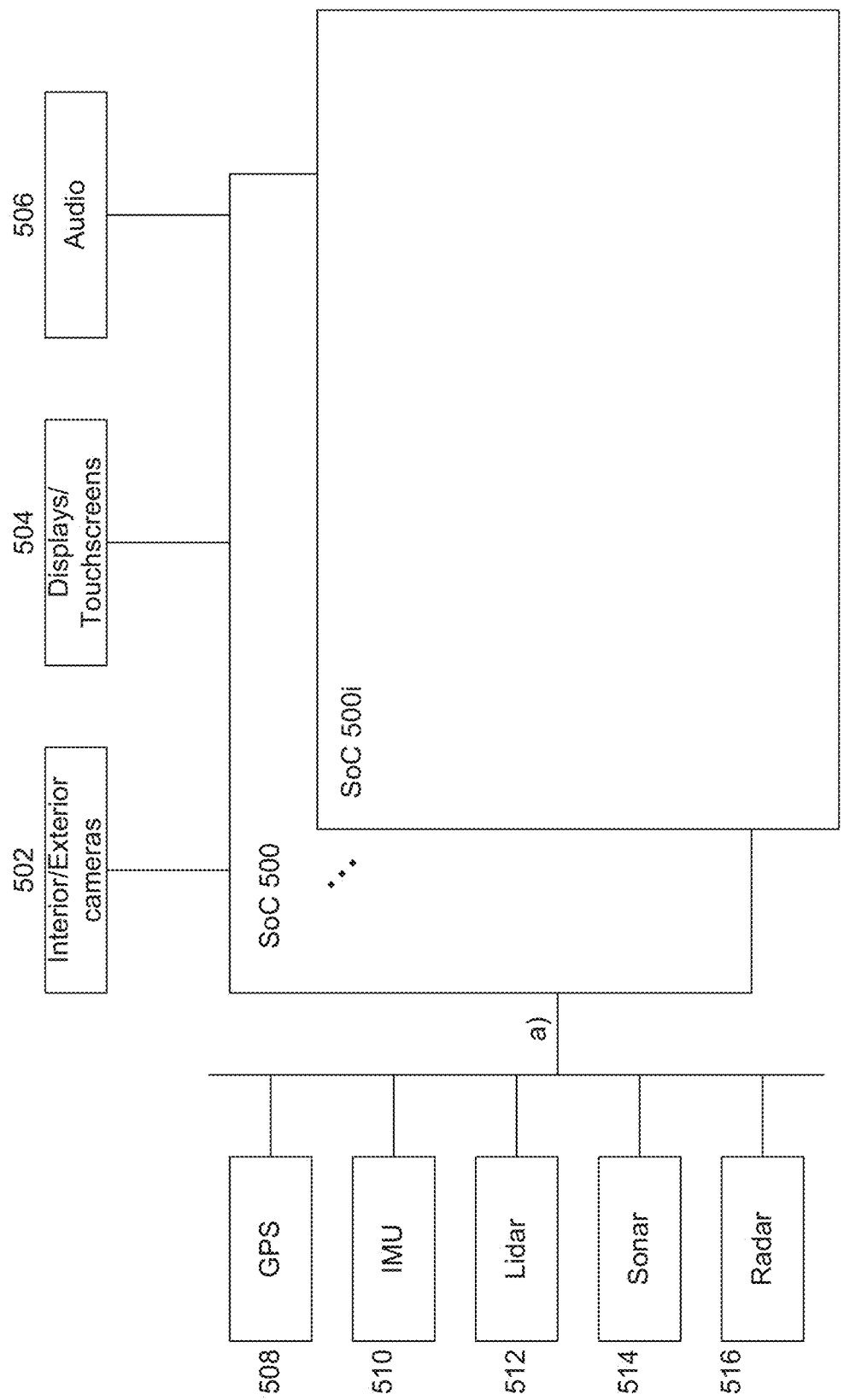
FIG. 5A is an illustration of a system on chip for controlling a vehicle, in accordance with an embodiment of the disclosure.

FIG. 5A is an illustration of a system on chip for controlling a vehicle, in accordance with an embodiment of the disclosure. Referring to FIG. 5A, there is shown a plurality of system on chip (SoC) 500 to 500*i*, each of which is a processor with enough support functionality on the same chip to be able to perform many functions by itself. For example, each of the SoCs 500 to 500*i* may have volatile and non-volatile memory, I/O support for standards like USB, and be able to perform some wireless communication, as well as other functions. Various embodiments may have different architectures with different amount of interfacing between/among the SoCs 500 to 500*i*. While there may be various embodiments with a plurality of SoCs 500 to 500*i* that may or may not be similar, some embodiments may only have a single SoC 500. Accordingly, various embodiments of the disclosure are not limited to a specific number of SoCs, nor whether the SoCs are similar or different.

Each of the SoCs 500 to 500*i* may be functionally connected to various sensors and input/output devices such as, for example, interior and exterior cameras 502, displays/touchscreens 504, audio input and/or output 506, GPS 508, inertial measurement unit (IMU) 510, lidar 512, sonar 514, and radar 516. The data from these sensors may be used, for example, to generate maps of the area surrounding the smart car 100. This may include other vehicles around the car, their speeds, their distances from the smart car 100, etc. There may also be pedestrians or non-motorized vehicles, as well as obstructions in the map. The map may also show traffic lights and whether the light is red, yellow, or green. With this information, the smart car 100 can provide guidance and warning to the driver, or control the smart car 100 if the driver is not responding to avoid a dangerous situation. This information may also be used to allow the smart car 100 to drive autonomously.

The map may be generated with data from the cameras 502, or with data from other sensors such as the lidar 512, the sonar 514, and/or the radar 516. Accordingly, one or more of the sensors may be used to generate the map, and the map may also be a 3-dimensional map.

Depending on a particular configuration, the SoC 500 may be connected to other functional blocks such as, for example, more memory and/or processors (including SoCs). Each of the SoCs 500 to 500i may also be connected to different types of sensors as well as different number of sensors. Multiple SoCs connected to multiple sensors may be to dedicate enough processing power for specific applications and/or to allow for redundancy in processing and/or sensing at the hardware level for sensors as well as the processors.

Figure 5B:
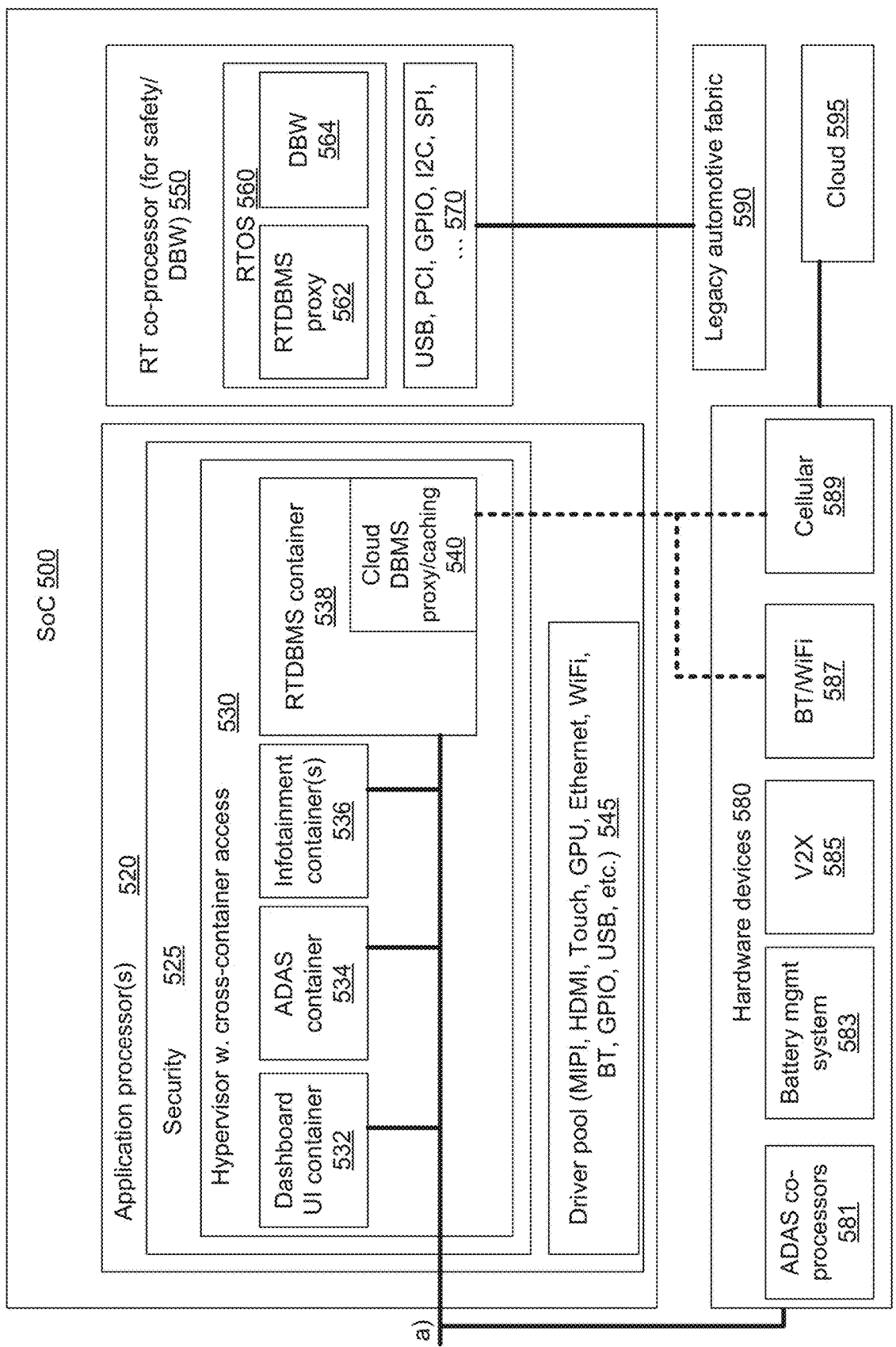
FIG. 5B is a block diagram of a system on chip for controlling a vehicle, in accordance with an embodiment of the disclosure.

FIG. 5B is a block diagram of a system on chip for controlling a vehicle, in accordance with an embodiment of the disclosure. Referring to FIG. 5B, there is shown the SoC 500 of FIG. 5A. While various SoCs can have different configurations, the SoC 500 may comprise one or more processors 520. A processor 520 may have software running on it, and some of the software may be the security software 525 to keep the smart car 100 operating safely and securely. The security software 525 may monitor other software, including the hypervisor 530. The hypervisor 530 may create various containers such as, for example, the dashboard user interface container 532, the ADAS container 534, the infotainment container 536, and the real-time database management system (RTDBMS) 538.

The RTDBMS 538 may be, for example, similar to the DBW and data hub 334, and may be able to connect to a cloud system 595 by means of DBMS 540. Accordingly, at least some of the data managed by the RTDBMS 538 may be stored in a cloud system 595. The RTDBMS 538 may connect to the cloud system 595 via, for example, Bluetooth, WiFi, and/or cellular communication using appropriate devices that support such communication.

These containers may be connected via a bus a) to some of the sensors shown in FIG. 5A, such as, for example, the GPS 508, the IMU 510, the lidar 512, the sonar 514, and the radar 516. The bus a) may also connect the containers to other systems and functions, such as, for example, hardware devices 580. The hardware devices 580 may comprise, for example, the ADAS co-processor(s) 581, the battery management system 583, V2X communication unit 585, and wireless functionality supporting, for example, Bluetooth, WiFi, and cellular communication by communication circuits 587 and 589.

The SoC 500 may also comprise a real time co-processor 550 that may be used primarily for safety concerns for the smart car 100 and for drive by wire (DBW) functionality of the smart car 100. The co-processor 550 may use a real-time operating system (RTOS) 560 that has an RTDBMS proxy 562 and DBW functions 564. The co-processor 550 may also have hardware and software that support various I/O standards such as USB, PCI, GPIO, I2C, SPI, etc. The co-processor 550 may use one of these I/O standards to connect to legacy automotive fabric 590 that may be present in the smart car 100.

Depending on the architecture and technology, each processor may have its own hypervisor, or there may be one hypervisor for multiple processors. Accordingly, an embodiment may have one hypervisor for the plurality of SoCs 500 to 500i.

If there are multiple hypervisors, a hypervisor may be able to detect software failure or a container failure, such as, for example, failure of a software driver. The hypervisor that detected the failure may then be able to trigger execution of similar software drivers running under a different hypervisor on a different processor. This can provide for software redundancy. Similarly, a prime hypervisor may be able to determine the status of various hypervisors in, for example, the smart car 100. Upon detecting the failure of, for example, a software driver, the prime hypervisor may trigger another hypervisor to execute a similar software driver to provide continuity.

Accordingly, the present architecture that can be used in the smart car 100 can support both legacy automotive fabric as well as modern automotive fabric for controlling the smart car 100 at least in part. The legacy automotive fabric includes the controller area network (CAN) first developed by the Society of Automotive Engineers, which has been used widely in automobiles is limiting for more advanced purposes.

Figure 6:
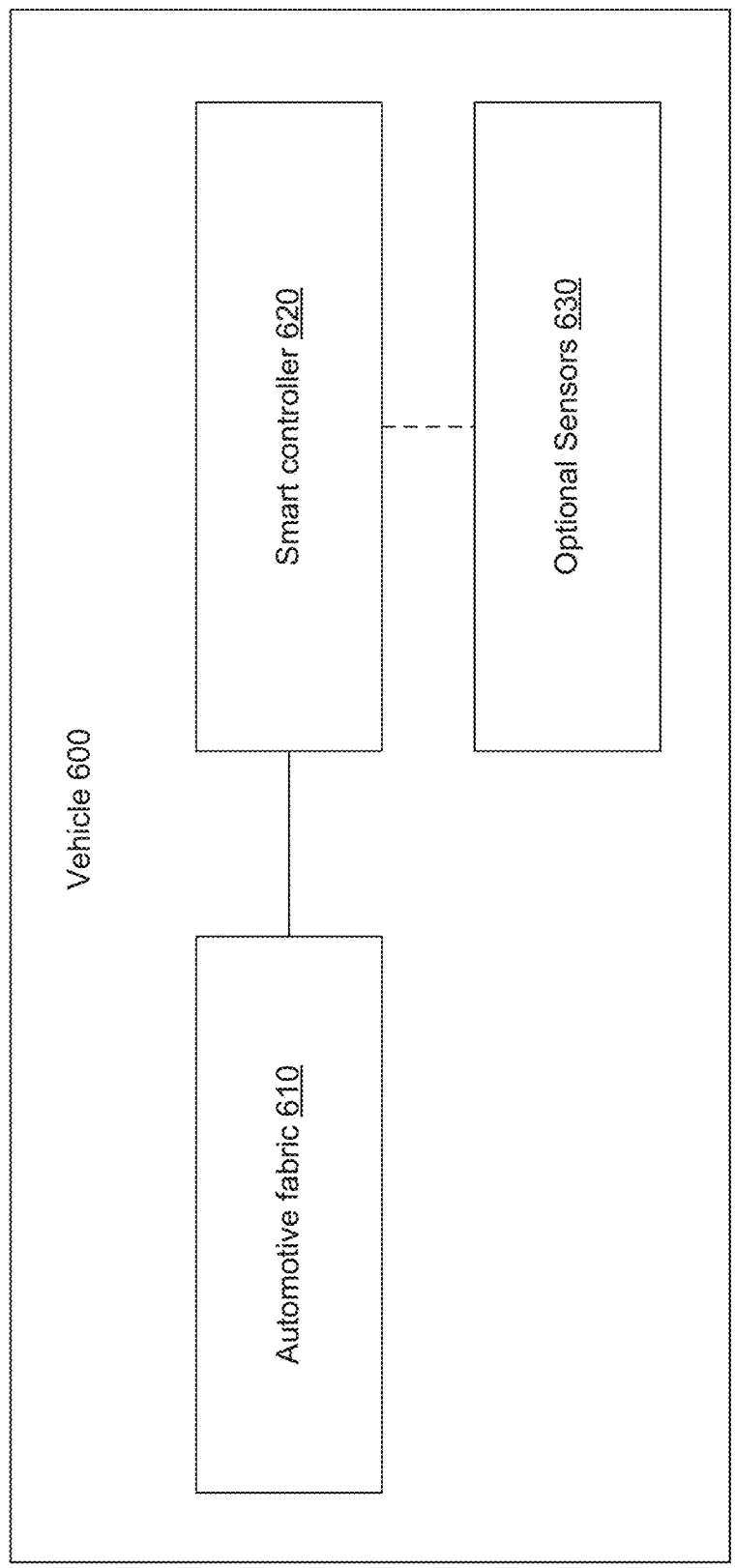
FIG. 6 is a block diagram of an example of an after-market device integrated with a vehicle, in accordance with an embodiment of the disclosure.

FIG. 6 is a block diagram of an example of an after-market device integrated with a vehicle, in accordance with an embodiment of the disclosure. Referring to FIG. 6, there is shown a vehicle 600 with an automotive fabric 610. The vehicle 600, while it may have some driver assist functionality, does not have the level of integration of a smart car 100 as described with respect to FIGS. 1A-5. A vehicle such as the vehicle 600 may still be able to acquire some of the smart car functionality of the smart car 100. This may be achieved, for example, with an after-market smart controller device 620.

The smart controller device 620 may be attached to the automotive fabric 610 by, for example, plugging in to the on-board diagnostic (OBD) port. While this may be a convenient place to attach to the automotive fabric 610, the smart controller device 620 may also be attached to the automotive fabric 610 at other points as needed.

In an embodiment, the smart controller device 620 may be in a monitoring mode where it passively monitors the performance of the vehicle 600 to determine the normal working conditions to in effect "calibrate" the various sensors and actuators. While not directly affecting the performance of the sensors or the actuators, the smart controller device 620 can learn to correlate sensor outputs to performance of the vehicle 600. After some amount of time, which may be signaled by the smart controller device 620 or determined by a mechanic or owner of the vehicle 600, the smart controller device 620 may be configured to go into an active mode where it will actively control one or more functions of the vehicle 600 or provide assistance for the driver of the vehicle 600.

When in the active mode, the smart controller device 620 may be connected to the automotive fabric 610 at other points to allow for control of the various actuators if the OBD port does not provide sufficient access to the actuators and/or sensors. The smart controller device 620 may also be connected to optional sensors 630 to allow for more information than is available from the vehicle 600.

Figure 7:
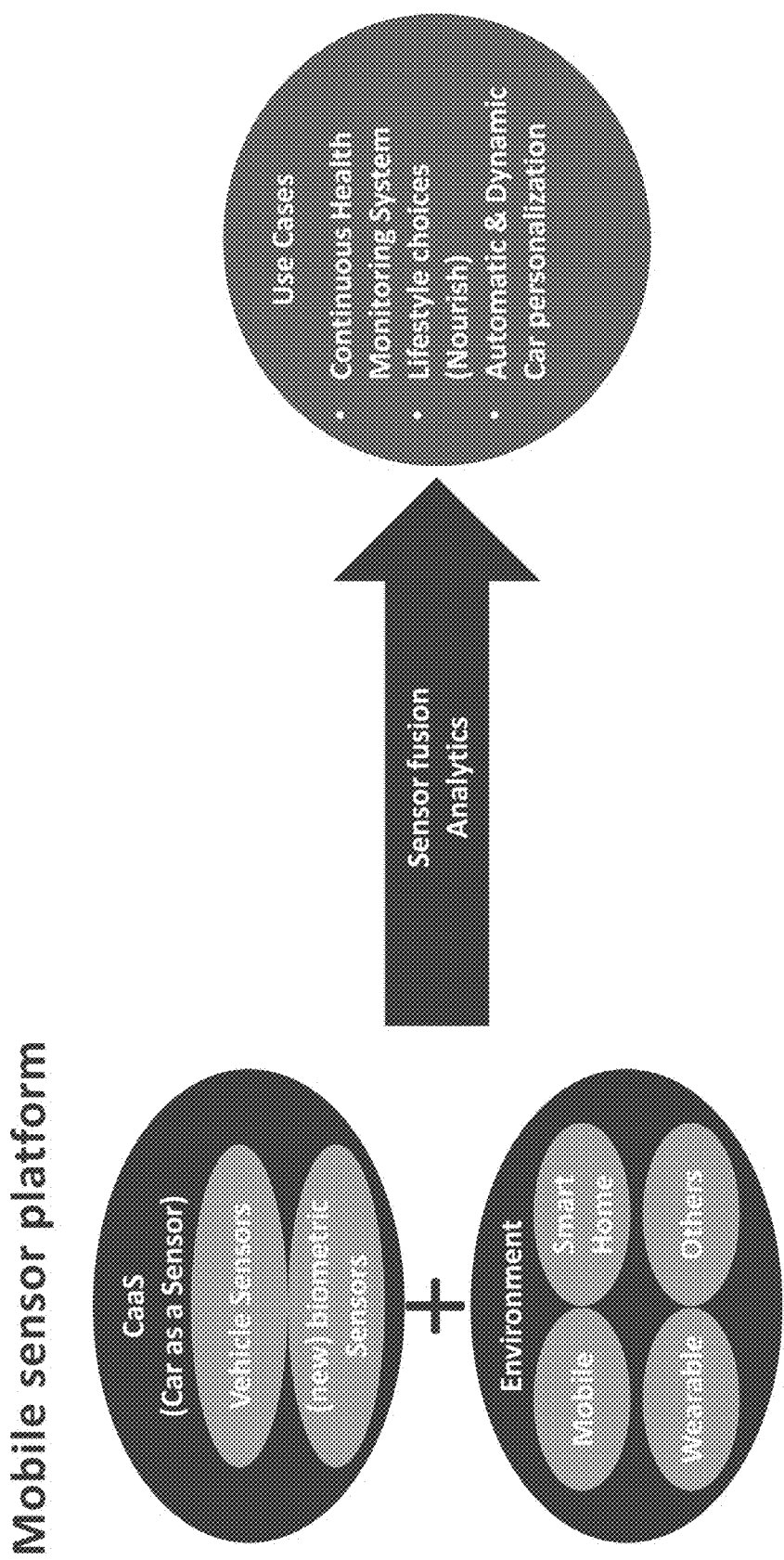
FIG. 7 is a diagram illustrating a mobile sensor platform, in accordance with an embodiment of the disclosure.

FIG. 7 is a diagram illustrating a mobile sensor platform, in accordance with an embodiment of the disclosure. Referring to FIG. 7, there is seen a melding of car as a sensor (CAAS) and the environment around the car. The environment may be at least as described in above paragraphs and figures. Accordingly, current vehicle sensors may be complemented by new additional sensors not existing in today's vehicles, which may be added to the vehicle after purchase of the vehicle. The additional vehicle sensors may be configured to, for example, make biometric measurements of the driver/passenger by including a full pull down of biometric detection including recognition for face, iris, fingerprint, voice, etc.

The environment may include all devices inside the vehicle that belongs to a driver/passenger as well as those sensors from the smart home of the driver/passenger, various wearable devices (smart wrist band, etc.) of the driver/passenger, or sensors that are part of a smart phone, other mobile devices, etc. Accordingly, the vehicle may be able to automatically synchronize information and functionally interact with any device the user approves such as, without limitation, one or more smart phone(s), PC(s), wearable device(s) and the like. Environment may also include data related to the driver/passenger (agenda, contact list, etc.) or also external data from services like weather or traffic, among others.

The CAAS may generate data, and that data may be combined with data from various sensors from the environment. These data can then undergo sensor analytic fusion as needed to provide various assistance to the driver/passenger. Accordingly, the vehicle may be a part of continuous health monitoring system (sensor in seat, steering wheel, phone, smart home) enabled to provide continuous monitoring of a driver/passenger.

Sensors for fusion may include, for example, ECG check, bioimpedance (body fat), breath spectrometry (ketosis), camera (HRV, mood, stress), air quality (pollution, tunnels), voice analysis (occupancy, mood of the occupants), occupant detection system (bladder+pressure), seat belt (respiration rate), head rest (EEG). By using these and other sensor data, the CAAS may be able to detect acute events (e.g., arrhythmia, seizures) and take appropriate actions such as calling the Emergency Call Number (911 in the US) or get into auto mode (and take the driver/riders to the nearest hospital). The continuous biometric data may then be made available to emergency medical technicians, nurses, and/or doctors using security arrangements to disallow providing information to unauthorized people/devices.

The continuous health monitoring service may be used as part of a health improvement program with any health or wellness related goal, for example weight loss, cardiac health, diabetes, hypertension, orthopedics, posture improvement and may use any combination of in-car sensors such as, for example, ECG monitor, bio-impedance sensor, image or video sensor (skin tone, heart rate), heart rate monitor, temperature sensor, blood oxygen monitor, blood pressure monitor, respiration monitor, accelerometer, in-seat bladder for weight measurement and/or a wearable sensor (such as a sensor in a watch) worn by the driver or passenger. The in-car monitors may be used to guide the user to achieve health goals in isolation or as part of a system of accompanying monitors such as wearable sensors, home based monitors (such as weight scales, blood pressure devices, cardiac monitors) or clinic based monitors (such as ECG's, imaging equipment). Progress toward health goals or immediate improvement in health status (such as lowering of blood pressure, decrease of heart rate, reduction of stress, improvement in blood oxygenation) may be assisted by functions of the car such as selection of music, lighting, route, location, social interaction based on mood (suggest calling/visiting friends, wife, family), among many use cases available The CAAS may also use contextual info from the vehicle or the environment (speed, steering, radio, windows, route options selected, car mode selected, occupancy, external conditions) to, for example, optimize car settings, and navigation route. Optimization of route may be to minimize environmental impact on allergic response. Various stimuli/relaxing items may be used by the vehicle to allow mood setting, and this may be automatic and dynamic vehicle personalization. For example, this may include playing appropriate music, releasing aroma, canceling irritating noises from the outside, etc. Some of this may use information about stress levels, mood, location, work and home interactions that may be gleaned from various sensors, as well as other sources such as information on the smart phones including emails, voice mails, etc. belonging to the driver/passenger.

Settings in the car may be adjusted to match driver and also provide secondary uses. Settings may include lighting, route, music, temperature, windows (adjusting the tint for brightness), aroma therapy, seat settings, etc. to make the driver/passenger more comfortable.

Authenticating a user (driver/passenger) can involve, for example, connecting to a health wearable device or a mobile device via secure arrangements. Accordingly, access to the capabilities of CAAS may be limited to authorized people. Additionally, this may allow parental control over minors or others who may not be trusted with the full capability of the CAAS. Control may be given to a subset or more of the vehicle's capabilities to various people.

A car may then be used as a hub for various lifestyle choices by capturing information from health objectives and other sensors (CAAS and environmental) to guide a user towards nutritional choices through the car. For example, the vehicle may make recommendations for restaurants or groceries when near a restaurant or grocery store at appropriate times for meals or shopping. The shopping may be when a user enters, for example, a note for groceries to buy or by gathering data from a smart fridge. The CAAS may make ingredients recommendations if the user searches for or notes a recipe.

The CAAS may also make recommendations for physical activity based on known history/interests of the user. With analysis of the various sensor data, the vehicle may also detect car sickness and compensate for that by opening windows, avoiding bumps, swerves, etc. to make the ride less contributory to motion sickness.

All the information gathered could be used to provide a car configurator to vehicle manufacturers and car dealers that may be based on the health profile of the driver/passenger purchasing a vehicle. One of the optional packages that could be provided or recommended when purchasing a vehicle may be a spot health checking.

Various embodiments of the disclosure may provide for a method to continuously monitor biometric signals of an occupant in a vehicle using one or more sensors in the vehicle, generating data results from data fusion of the biometric signals with other sensor signals received from one or more of first electronic devices in the vehicle and one or more second electronic devices external to the vehicle. The data results may be used to determine, for example, independently of the occupant, one or more actions to take on behalf of the occupant. The vehicle may perform the one or more actions independently of the occupant.

The method may also comprise receiving the biometric signals from one or more of an ECG sensor, a bio-impedance sensor, a breath spectrometer, a respiration detector, a temperature sensor, a blood oxygen monitor, a blood pressure monitor, and an EEG sensor. The first electronic devices may comprise a microphone, and signals from the microphone may be processed for voice stress analysis of the occupant. The first electronic devices may comprise a camera, and signals from the camera may be processed to determine a stress level of the occupant.

The one or more second electronic devices may comprise home based equipment such as, for example, a weight scale, a blood pressure monitor, a cardiac monitor, smart appliances, etc. The one or more second electronic devices may also comprise medical facility based equipment such as, for example, an ECG monitor and an imaging equipment.

When the data results indicate an acute physical condition, the one or more actions may comprise the vehicle calling an emergency number. When the vehicle is an autonomous vehicle, and when the data results indicate an acute physical condition, the one or more actions may comprise, for example, the vehicle autonomously driving to a nearest medical facility able to handle the acute physical condition. Furthermore, when the data results indicate an acute physical condition, the one or more actions may comprise the vehicle providing at least some of the biometric signals for use by medical personnel.

Performing the one or more actions may relate to one or more health goals of the occupant, where the health goals may comprise, for example, lowering blood pressure, decreasing heart rate, reducing stress, and improving blood oxygenation. The one or more actions may comprise, for example, selecting music to be played for the occupant, adjusting internal lighting in the vehicle, adjusting a tint of a window for brightness, adjusting opening the window to one of various states fully closed to fully open, releasing a particular aroma, suggesting one or more specific persons to talk to, routing a travel path of the vehicle to reduce exposure to allergens, canceling external noise, adjusting internal temperature of the vehicle, adjusting suspension settings for the vehicle, making recommendations for groceries at a grocery store and making recommendations for meals at a restaurant.

Various embodiments of the disclosure may provide for a system comprising one or more sensors in a vehicle configured to continuously monitor biometric signals of an occupant in the vehicle, one or more processors configured to generate data results from data fusion of the biometric signals with other sensor signals that are received from one or more of: one or more first electronic devices in the vehicle, and one or more second electronic devices external to the vehicle. The data results may be used to determine, independently of the occupant, one or more actions to take on behalf of the occupant independently of the occupant.

The sensors may comprise, for example, an ECG sensor, a bio-impedance sensor, a breath spectrometer, a respiration detector, a temperature sensor, a blood oxygen monitor, a blood pressure monitor, and an EEG sensor.

The first electronic devices may comprise a microphone configured to output microphone signals, and the one or more processors may be configured to process the microphone signals for voice stress analysis of the occupant. The first electronic devices may also comprise a camera configured to output camera signals, and the one or more processors may be configured to process the camera signals to determine a stress level of the occupant.

The second electronic devices may comprise home based equipment such as, for example, a weight scale, a blood pressure monitor, a cardiac monitor, smart appliances, etc., and medical facility based equipment such as, for example, an ECG monitor, an imaging equipment, etc.

When the data results indicate an acute physical condition, the one or more actions may comprise the vehicle calling an emergency number. When the vehicle is an autonomous vehicle, and when the data results indicate an acute physical condition, the one or more actions may comprise the vehicle autonomously driving to a nearest medical facility able to handle the acute physical condition. Furthermore, when the data results indicate an acute physical condition, the one or more actions may comprise the vehicle providing at least some of the biometric signals for use by medical personnel.

The one or more actions may relate to, for example, one or more health goals of the occupant, where the health goals comprise lowering blood pressure, decreasing heart rate, reducing stress, and improving blood oxygenation. For example, the one or more actions may comprise selecting music to be played for the occupant, adjusting internal lighting in the vehicle, adjusting a tint of a window for brightness, adjusting opening the window to one of various states fully closed to fully open, releasing a particular aroma; suggesting one or more specific persons to talk to, routing a travel path of the vehicle to reduce exposure to allergens, canceling external noise, adjusting internal temperature of the vehicle, adjusting suspension settings for the vehicle, making recommendations for groceries at a grocery store; and making recommendations for meals at a restaurant.

Accordingly, in addition to other functions, the system overall may serve as both a vehicle performance and occupant health "black box" that continually captures, accumulates and retains both vehicle performance and multi-parameter occupant health and/or biometric (including but not limited to, face, iris, finger-print, voice, and the like) data together with any corresponding inside-the-vehicle and external-to-the-vehicle environmental data such that the system can "roll back the tape" as desired to analyze such captured, accumulated and retained data. While some specific items may have been mentioned, an embodiment of the present disclosure need not be limited by those items. For example, the CAAS may be configured for one person or multiple people.

Therefore, it can be seen that the present disclosure relates to a man-made vehicle being responsive to its environment to help guide itself and/or others for locomotion, whether any of these devices are operating on their own or under human control. The human control may be by a human in the vehicle, or remote control by a human. In some cases, the remote control may be by another man-made device. Additionally, the smart car 100 may have a drone that can be sent off to gather further information. This may be the case if there are not many other sources of information such as, for example, other smart cars. The drone may then fly ahead to provide information that may be beyond the range of the sensors of the smart car 100. The drone may also provide views of scenery not available from the smart car 100.

A vehicle refers generally to a man-made object such as, for example, land-based vehicles, drones, robots, airplanes, water-based vehicles such as boats, submarines, under water exploration vehicles, etc., and extra-terrestrial vehicles (spacecrafts, various exploration vehicles such as, for example, the Mars Rover).

While various embodiments have been described for functional uses of the present disclosure, it should be understood that the data center capability of the various embodiments allows the implementation of the various embodiments. The data center capability refers to the ability to collect data, analyze data, perform data fusion of relevant data, and determine actions to take with the analyzed/fusion data. Additionally, the data center capability of the disclosure also allows sharing with other devices/platforms any of the collected data, the analyzed data, the fusion data, and the determined actions directly with the other devices/platforms or via a cloud platform.

Various embodiments of the disclosure may be written as computer programs and may be implemented in general-use digital computers that execute the programs using a non-transitory computer-readable recording medium.

Non-transitory computer-readable recording medium may include, for example, magnetic storage media (e.g., ROM, floppy disks, hard disks, etc.), optical recording media (e.g., CD-ROMs, or DVDs), etc.

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What are claimed:

1. A method comprising:
   continuously monitoring biometric signals of an occupant in a vehicle using one or more sensors in the vehicle;
   generating data results from data fusion of the biometric signals with other sensor signals received from one or more of: one or more first electronic devices in the vehicle, and one or more second electronic devices external to the vehicle;
   using the data results to determine one or more actions to take on behalf of the occupant; and
   the vehicle performing the one or more actions;
   wherein the one or more second electronic devices comprises one of: home based equipment, and medical facility based equipment;
   wherein the home based equipment comprises one of: a weight scale, a blood pressure monitor, a cardiac monitor, and a smart appliance.

2. The method of claim 1, comprising receiving the biometric signals from one of: an ECG sensor, a bio-impedance sensor, a breath spectrometer, a respiration detector, a temperature sensor, a blood oxygen monitor, a blood pressure monitor, and an EEG sensor.

3. The method of claim 1, wherein the first electronic devices comprise a microphone, and signals from the microphone are processed for voice stress analysis of the occupant.

4. The method of claim 1, wherein the first electronic devices comprise a camera, and signals from the camera are processed to determine a stress level of the occupant.

5. The method of claim 1, wherein the medical facility based equipment comprises one of: an ECG monitor, and an imaging equipment.

6. The method of claim 1, wherein, when the data results indicate an acute physical condition, the one or more actions comprise the vehicle calling an emergency number.

7. The method of claim 1, wherein the vehicle is an autonomous vehicle, and when the data results indicate an acute physical condition, the one or more actions comprise the vehicle autonomously driving to a medical facility.

8. The method of claim 1, wherein when the data results indicate an acute physical condition, the one or more actions comprise the vehicle providing at least some of the biometric signals for use by medical personnel.

9. The method of claim 1, wherein performing the one or more actions relate to one or more health goals of the occupant, the health goals comprising one of: lowering blood pressure, decreasing heart rate, reducing stress, and improving blood oxygenation.

10. The method of claim 9, wherein the one or more actions comprise:
    selecting music to be played for the occupant;
    adjusting internal lighting in the vehicle;
    adjusting a tint of a window for brightness;
    adjusting opening the window to one of various states fully closed to fully open;
    releasing a particular aroma;
    suggesting one or more specific persons to talk to;
    routing a travel path of the vehicle to reduce exposure to allergens;
    canceling external noise;
    adjusting internal temperature of the vehicle;
    adjusting suspension settings for the vehicle;
    making recommendations for groceries at a grocery store; and
    making recommendations for meals at a restaurant.

11. A system comprising:
    one or more sensors in a vehicle configured to continuously monitor biometric signals of an occupant in the vehicle;
    one or more processors configured to:
       generate data results from data fusion of the biometric signals with other sensor signals received from one or more of: one or more first electronic devices in the vehicle, and one or more second electronic devices external to the vehicle; and
       using the data results to determine one or more actions to take on behalf of the occupant; and
    the vehicle performing the one or more actions;
    wherein the vehicle is an autonomous vehicle, and when the data results indicate an acute physical condition, the one or more actions comprise the vehicle autonomously driving to a medical facility.

12. The system of claim 11, wherein the biometric sensors comprise one of: an ECG sensor, a bio-impedance sensor, a breath spectrometer, a respiration detector, a temperature sensor, a blood oxygen monitor, a blood pressure monitor, and an EEG sensor.

13. The system of claim 11, wherein the first electronic devices comprise:
    a microphone configured to output microphone signals, and the one or more processors are configured to process the microphone signals for voice stress analysis of the occupant; and
    a camera configured to output camera signals, and the one or more processors are configured to process the camera signals to determine a stress level of the occupant.

14. The system of claim 11, wherein the one or more second electronic devices comprise:
    home based equipment comprising one of: a weight scale, a blood pressure monitor, a cardiac monitor, and a smart appliance; and
    medical facility based equipment comprising one of: an ECG monitor, and imaging equipment.

15. The system of claim 11, wherein, when the data results indicate an acute physical condition, the one or more actions comprise the vehicle calling an emergency number.

16. The system of claim 11, wherein when the data results indicate an acute physical condition, the one or more actions comprise the vehicle providing at least some of the biometric signals for use by medical personnel.

17. The system of claim 11, wherein performing the one or more actions relate to one or more health goals of the occupant, the health goals comprising one of: lowering blood pressure, decreasing heart rate, reducing stress, and improving blood oxygenation.

18. The system of claim 17, wherein the one or more actions comprise:
- selecting music to be played for the occupant;
- adjusting internal lighting in the vehicle;
- adjusting a tint of a window for brightness;
- adjusting opening the window to one of various states fully closed to fully open;
- releasing a particular aroma;
- suggesting one or more specific persons to talk to;
- routing a travel path of the vehicle to reduce exposure to allergens;
- canceling external noise;
- adjusting internal temperature of the vehicle;
- adjusting suspension settings for the vehicle;
- making recommendations for groceries at a grocery store; and
- making recommendations for meals at a restaurant.

* * * * *